(12) United States Patent
Kim et al.

(10) Patent No.: US 12,630,629 B2
(45) Date of Patent: May 19, 2026

(54) ANTI-IGSF1 ANTIBODY AND USE THEREOF

(71) Applicant: WELLMARKER BIO CO., LTD., Seoul (KR)

(72) Inventors: Seong-Rak Kim, Seoul (KR); Hye-Jin Son, Seoul (KR); Mi-So Lee, Seoul (KR); Ha-Na Kim, Seoul (KR); Jun-Hyung Lee, Seoul (KR); Won-Hwa Shin, Seoul (KR)

(73) Assignee: Wellmarker Bio Co., Ltd., Seoul (KR)

( * ) Notice: Subject to any disclaimer, the term of this patent is extended or adjusted under 35 U.S.C. 154(b) by 698 days.

(21) Appl. No.: 17/997,019

(22) PCT Filed: Aug. 20, 2021

(86) PCT No.: PCT/KR2021/011139
§ 371 (c)(1),
(2) Date: Oct. 24, 2022

(87) PCT Pub. No.: WO2023/022271
PCT Pub. Date: Feb. 23, 2023

(65) Prior Publication Data
US 2024/0262906 A1 Aug. 8, 2024

(51) Int. Cl.
| | |
|---|---|
| *A61P 35/00* | (2006.01) |
| *A61K 39/00* | (2006.01) |
| *C07K 16/28* | (2006.01) |

(52) U.S. Cl.
CPC .......... *C07K 16/2803* (2013.01); *A61K 39/00* (2013.01); *A61P 35/00* (2018.01); *A61K 2039/505* (2013.01); *C07K 2317/565* (2013.01)

(58) Field of Classification Search
CPC .......... C07K 16/2803; C07K 2317/565; C07K 2317/21; C07K 2317/73; C07K 2317/92; A61K 39/00; A61K 2039/505; A61P 35/00; C12N 15/85
See application file for complete search history.

(56) References Cited

U.S. PATENT DOCUMENTS

| | | | |
|---|---|---|---|
| 7,138,501 B2 * | 11/2006 | Ruben ................ | C07K 16/2875 |
| | | | 530/391.1 |
| 11,186,873 B2 | 11/2021 | Jin et al. | |
| 2009/0053243 A1 | 2/2009 | Kurosawa et al. | |

OTHER PUBLICATIONS

Cancer risk and prevention. American Cancer Society. Accessed Mar. 21, 2025. https://www.cancer.org/cancer/risk-prevention.html. Internet. Wayback Machine (Year: 2025).*
Bernard et al., "From Consternation to Revelation: Discovery of a Role for IGSF1 in Pituitary Control of Thyroid Function," *Journal of the Endocrine Society* 2(3):220-231, Mar. 2018.

(Continued)

*Primary Examiner* — Joanne Hama
*Assistant Examiner* — Hannah Sunshine
(74) *Attorney, Agent, or Firm* — Seed IP Law Group LLP

(57) ABSTRACT
A novel antibody that specifically binds to IGSF1 and a pharmaceutical composition for preventing or treating cancer, comprising the same as an active ingredient. Specifically, an antibody that binds to the C-terminus of IGSF1. Therefore, the anti-IGSF1 antibody may be utilized as an anticancer agent for effectively treating cancer in which IGSF1 is overexpressed.

14 Claims, 9 Drawing Sheets
Specification includes a Sequence Listing.

(56)                References Cited

OTHER PUBLICATIONS

Guan et al., "IGSF1: A novel oncogene regulates the thyroid cancer progression," *Cell Biochem Funct*. 37:516-524, 2019.

Wang et al., "The short mRNA isoform of the immunoglobulin superfamily, member 1 gene encodes an intracellular glycoprotein," *PLoS One*:1-11, Jul. 7, 2017.

Faucz et al., "Is IGSF1 involved in human pituitary tumor formation?," Endocrine-Related Cancer 22(1):47-54, Feb. 2015 (NIH Public Access Author Manuscript, available in PMC Apr. 1, 2015). (13 pages).

Koh et al., "The Immune Suppressor IGSF1 as a Potential Target for Cancer Immunotherapy," Cancer Immunology Research 12(4):491-507, Apr. 2024 [Published online Jan. 30, 2024]. (17 pages).

* cited by examiner

TILs (%)

NCI-H292 MOCK Tumor    NCI-H292 IGSF1 O/E Tumor

* ▲ - TILs    - Cancer lysis

| | WM-A1-3389 |
|---|---|
| Kd | $2.2 \times 10^{-11}$ |
| R squared | 0.9933 |

*In vitro* 3D co-culture
TILs (Tumor-Infiltrating Lymphocytes) analysis

NCI-H292 IGSF1 O/E+PBMC

IgG                                    WM-A1-3389

| | WM-A1-3389 |
|---|---|
| Dose (mg/kg) | 10 |
| TGI (%) | 65.2 ± 2.1 |
| P-Value | 0.0000 (***) |

Representative IGSF1 expression analysis results
(lung cancer patient tissue)

SEQUENCE LISTING

```
<160> NUMBER OF SEQ ID NOS: 24

<210> SEQ ID NO 1
<211> LENGTH: 8
<212> TYPE: PRT
<213> ORGANISM: Artificial Sequence
<220> FEATURE:
<223> OTHER INFORMATION: H-CDR1 of WM-A1-3389

<400> SEQUENCE: 1

Gly Gly Thr Phe Ser Thr Tyr Ala
1               5

<210> SEQ ID NO 2
```

```
<211> LENGTH: 8
<212> TYPE: PRT
<213> ORGANISM: Artificial Sequence
<220> FEATURE:
<223> OTHER INFORMATION: H-CDR2 of WM-A1-3389

<400> SEQUENCE: 2

Ile Ile Pro Phe Val Gly Thr Val
1               5

<210> SEQ ID NO 3
<211> LENGTH: 11
<212> TYPE: PRT
<213> ORGANISM: Artificial Sequence
<220> FEATURE:
<223> OTHER INFORMATION: H-CDR3 of WM-A1-3389

<400> SEQUENCE: 3

Val Arg Asp Gly Gly Arg Ser Tyr Phe Asp Ser
1               5                   10

<210> SEQ ID NO 4
<211> LENGTH: 8
<212> TYPE: PRT
<213> ORGANISM: Artificial Sequence
<220> FEATURE:
<223> OTHER INFORMATION: L-CDR1 of WM-A1-3389

<400> SEQUENCE: 4

Thr Ser Asn Ile Gly Ser Asn Leu
1               5

<210> SEQ ID NO 5
<211> LENGTH: 3
<212> TYPE: PRT
<213> ORGANISM: Artificial Sequence
<220> FEATURE:
<223> OTHER INFORMATION: L-CDR2 of WM-A1-3389

<400> SEQUENCE: 5

Asp Asn His
1

<210> SEQ ID NO 6
<211> LENGTH: 11
<212> TYPE: PRT
<213> ORGANISM: Artificial Sequence
<220> FEATURE:
<223> OTHER INFORMATION: L-CDR3 of WM-A1-3389

<400> SEQUENCE: 6

Val Ala Trp Asp Asp Ser Leu Asn Gly Tyr Val
1               5                   10

<210> SEQ ID NO 7
<211> LENGTH: 118
<212> TYPE: PRT
<213> ORGANISM: Artificial Sequence
<220> FEATURE:
<223> OTHER INFORMATION: Variable region of heavy chain of WM-A1-3389

<400> SEQUENCE: 7

Gln Val Gln Leu Val Gln Ser Gly Ala Glu Val Lys Arg Pro Gly Ser
1               5                   10                  15

Ser Val Lys Val Ser Cys Lys Ala Ser Gly Gly Thr Phe Ser Thr Tyr
            20                  25                  30
```

-continued

```
Ala Ile Ser Trp Val Arg Gln Ala Pro Gly Gln Gly Leu Glu Trp Met
        35                  40                  45

Gly Arg Ile Ile Pro Phe Val Gly Thr Val Asp Tyr Ala Gln Lys Phe
    50                  55                  60

Gln Asp Arg Val Thr Ile Thr Ala Asp Lys Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Val Arg Asp Gly Gly Arg Ser Tyr Phe Asp Ser Trp Gly Pro Gly Ile
            100                 105                 110

Leu Val Thr Val Ser Ser
        115
```

```
<210> SEQ ID NO 8
<211> LENGTH: 110
<212> TYPE: PRT
<213> ORGANISM: Artificial Sequence
<220> FEATURE:
<223> OTHER INFORMATION: Variable region of light chain of WM-A1-3389

<400> SEQUENCE: 8

Gln Phe Val Leu Thr Gln Pro Pro Ser Val Ser Ala Ala Pro Gly Gln
1               5                   10                  15

Asp Val Ile Ile Ser Cys Ser Gly Asn Thr Ser Asn Ile Gly Ser Asn
            20                  25                  30

Leu Val Ser Trp Phe Gln Gln Phe Pro Glu Thr Ala Pro Lys Leu Leu
        35                  40                  45

Ile Tyr Asp Asn His Lys Arg Pro Ser Gly Ile Ser Asp Arg Phe Ser
    50                  55                  60

Gly Thr Lys Ser Gly Thr Ser Ala Ser Leu Ala Ile Ser Gly Leu Gln
65                  70                  75                  80

Ser Glu Asp Glu Ala Asp Tyr Tyr Cys Val Ala Trp Asp Asp Ser Leu
                85                  90                  95

Asn Gly Tyr Val Phe Gly Thr Gly Thr Lys Val Thr Val Leu
            100                 105                 110
```

```
<210> SEQ ID NO 9
<211> LENGTH: 354
<212> TYPE: DNA
<213> ORGANISM: Artificial Sequence
<220> FEATURE:
<223> OTHER INFORMATION: Polynucleotide coding variable region of heavy
      chain of WM-A1-3389

<400> SEQUENCE: 9
caggtgcagc tggtacagtc tggggctgag gtgaagaggc ctgggtcctc ggtgaaggtc      60
tcctgcaagg cttctggagg caccttcagc acctatgcta tcagctgggt gcgacaggcc     120
cctggacaag gcttgagtg gatgggaagg atcatccctt tcgttggtac agtagactac     180
gcacagaagt tccaggacag agtcacaatt accgcggaca atccacgaa cacagcctac      240 atggagctga gcagcctgag atctgaggac acggccgtgt attactgtgt gagagatggg     300
ggccgtagtt attttgactc ctggggcccg ggaatcctgg tcaccgtctc ctca          354
```

```
<210> SEQ ID NO 10
<211> LENGTH: 330
<212> TYPE: DNA
<213> ORGANISM: Artificial Sequence
<220> FEATURE:
<223> OTHER INFORMATION: Polynucleotide coding variable region of light
```

```
        chain of WM-A1-3389

<400> SEQUENCE: 10
cagttcgtgc tgactcagcc gccctcagtc tctgcggccc cagggcagga cgtcatcatc      60
tcttgctctg gaaacacttc caacattggg agtaaccttg tctcctggtt ccagcaattc     120
ccagagacag cccccaaact cctgatttat gacaatcata agcgaccctc aggaatttct     180
gaccgattct ctggcaccaa gtctggtacc tcagcctccc tggccatcag tgggctccag     240
tctgaggatg aggctgatta ttactgtgtg gcatgggatg acagtctgaa tggttatgtc     300
ttcggaactg ggaccaaggt caccgtccta                                      330

<210> SEQ ID NO 11
<211> LENGTH: 25
<212> TYPE: PRT
<213> ORGANISM: Artificial Sequence
<220> FEATURE:
<223> OTHER INFORMATION: H-FR1 of WM-A1-3389

<400> SEQUENCE: 11

Gln Val Gln Leu Val Gln Ser Gly Ala Glu Val Lys Arg Pro Gly Ser
1               5                   10                  15

Ser Val Lys Val Ser Cys Lys Ala Ser
            20                  25

<210> SEQ ID NO 12
<211> LENGTH: 17
<212> TYPE: PRT
<213> ORGANISM: Artificial Sequence
<220> FEATURE:
<223> OTHER INFORMATION: H-FR2 of WM-A1-3389

<400> SEQUENCE: 12

Ile Ser Trp Val Arg Gln Ala Pro Gly Gln Gly Leu Glu Trp Met Gly
1               5                   10                  15

Arg

<210> SEQ ID NO 13
<211> LENGTH: 38
<212> TYPE: PRT
<213> ORGANISM: Artificial Sequence
<220> FEATURE:
<223> OTHER INFORMATION: H-FR3 of WM-A1-3389

<400> SEQUENCE: 13

Asp Tyr Ala Gln Lys Phe Gln Asp Arg Val Thr Ile Thr Ala Asp Lys
1               5                   10                  15

Ser Thr Asn Thr Ala Tyr Met Glu Leu Ser Ser Leu Arg Ser Glu Asp
            20                  25                  30

Thr Ala Val Tyr Tyr Cys
        35

<210> SEQ ID NO 14
<211> LENGTH: 11
<212> TYPE: PRT
<213> ORGANISM: Artificial Sequence
<220> FEATURE:
<223> OTHER INFORMATION: H-FR4 of WM-A1-3389

<400> SEQUENCE: 14

Trp Gly Pro Gly Ile Leu Val Thr Val Ser Ser
1               5                   10
```

```
<210> SEQ ID NO 15
<211> LENGTH: 25
<212> TYPE: PRT
<213> ORGANISM: Artificial Sequence
<220> FEATURE:
<223> OTHER INFORMATION: L-FR1 of WM-A1-3389

<400> SEQUENCE: 15

Gln Phe Val Leu Thr Gln Pro Pro Ser Val Ser Ala Ala Pro Gly Gln
1               5                   10                  15

Asp Val Ile Ile Ser Cys Ser Gly Asn
            20                  25

<210> SEQ ID NO 16
<211> LENGTH: 17
<212> TYPE: PRT
<213> ORGANISM: Artificial Sequence
<220> FEATURE:
<223> OTHER INFORMATION: L-FR2 of WM-A1-3389

<400> SEQUENCE: 16

Val Ser Trp Phe Gln Gln Phe Pro Glu Thr Ala Pro Lys Leu Leu Ile
1               5                   10                  15

Tyr

<210> SEQ ID NO 17
<211> LENGTH: 36
<212> TYPE: PRT
<213> ORGANISM: Artificial Sequence
<220> FEATURE:
<223> OTHER INFORMATION: L-FR3 of WM-A1-3389

<400> SEQUENCE: 17

Lys Arg Pro Ser Gly Ile Ser Asp Arg Phe Ser Gly Thr Lys Ser Gly
1               5                   10                  15

Thr Ser Ala Ser Leu Ala Ile Ser Gly Leu Gln Ser Glu Asp Glu Ala
            20                  25                  30

Asp Tyr Tyr Cys
        35

<210> SEQ ID NO 18
<211> LENGTH: 10
<212> TYPE: PRT
<213> ORGANISM: Artificial Sequence
<220> FEATURE:
<223> OTHER INFORMATION: L-FR4 of WM-A1-3389

<400> SEQUENCE: 18

Phe Gly Thr Gly Thr Lys Val Thr Val Leu
1               5                   10

<210> SEQ ID NO 19
<211> LENGTH: 756
<212> TYPE: PRT
<213> ORGANISM: Artificial Sequence
<220> FEATURE:
<223> OTHER INFORMATION: IGSF1

<400> SEQUENCE: 19

Glu Glu Thr Glu Ile Val Met Pro Thr Pro Lys Pro Glu Leu Trp Ala
1               5                   10                  15

Glu Thr Asn Phe Pro Leu Ala Pro Trp Lys Asn Leu Thr Leu Trp Cys
            20                  25                  30
```

-continued

```
Arg Ser Pro Ser Gly Ser Thr Lys Glu Phe Val Leu Leu Lys Asp Gly
        35              40              45

Thr Gly Trp Ile Ala Thr Arg Pro Ala Ser Glu Gln Val Arg Ala Ala
    50              55              60

Phe Pro Leu Gly Ala Leu Thr Gln Ser His Thr Gly Ser Tyr His Cys
65              70              75              80

His Ser Trp Glu Glu Met Ala Val Ser Glu Pro Ser Glu Ala Leu Glu
                85              90              95

Leu Val Gly Thr Asp Ile Leu Pro Lys Pro Val Ile Ser Ala Ser Pro
                100             105             110

Thr Ile Arg Gly Gln Glu Leu Gln Leu Arg Cys Lys Gly Trp Leu Ala
            115             120             125

Gly Met Gly Phe Ala Leu Tyr Lys Glu Gly Glu Gln Glu Pro Val Gln
    130             135             140

Gln Leu Gly Ala Val Gly Arg Glu Ala Phe Phe Thr Ile Gln Arg Met
145             150             155             160

Glu Asp Lys Asp Glu Gly Asn Tyr Ser Cys Arg Thr His Thr Glu Lys
                165             170             175

Arg Pro Phe Lys Trp Ser Glu Pro Ser Glu Pro Leu Glu Leu Val Ile
            180             185             190

Lys Glu Met Tyr Pro Lys Pro Phe Phe Lys Thr Trp Ala Ser Pro Val
        195             200             205

Val Thr Pro Gly Ala Arg Val Thr Phe Asn Cys Ser Thr Pro His Gln
    210             215             220

His Met Ser Phe Ile Leu Tyr Lys Asp Gly Ser Glu Ile Ala Ser Ser
225             230             235             240

Asp Arg Ser Trp Ala Ser Pro Gly Ala Ser Ala Ala His Phe Leu Ile
            245             250             255

Ile Ser Val Gly Ile Gly Asp Gly Gly Asn Tyr Ser Cys Arg Tyr Tyr
            260             265             270

Asp Phe Ser Ile Trp Ser Glu Pro Ser Asp Pro Val Glu Leu Val Val
        275             280             285

Thr Glu Phe Tyr Pro Lys Pro Thr Leu Leu Ala Gln Pro Gly Pro Val
    290             295             300

Val Phe Pro Gly Lys Ser Val Ile Leu Arg Cys Gln Gly Thr Phe Gln
305             310             315             320

Gly Met Arg Phe Ala Leu Leu Gln Glu Gly Ala His Val Pro Leu Gln
            325             330             335

Phe Arg Ser Val Ser Gly Asn Ser Ala Asp Phe Leu Leu His Thr Val
            340             345             350

Gly Ala Glu Asp Ser Gly Asn Tyr Ser Cys Ile Tyr Tyr Glu Thr Thr
            355             360             365

Met Ser Asn Arg Gly Ser Tyr Leu Ser Met Pro Leu Met Ile Trp Val
    370             375             380

Thr Asp Thr Phe Pro Lys Pro Trp Leu Phe Ala Glu Pro Ser Ser Val
385             390             395             400

Val Pro Met Gly Gln Asn Val Thr Leu Trp Cys Arg Gly Pro Val His
            405             410             415

Gly Val Gly Tyr Ile Leu His Lys Glu Gly Glu Ala Thr Ser Met Gln
            420             425             430

Leu Trp Gly Ser Thr Ser Asn Asp Gly Ala Phe Pro Ile Thr Asn Ile
        435             440             445

Ser Gly Thr Ser Met Gly Arg Tyr Ser Cys Cys Tyr His Pro Asp Trp
```

```
            450                 455                 460

Thr Ser Ser Ile Lys Ile Gln Pro Ser Asn Thr Leu Glu Leu Leu Val
465                 470             475                 480

Thr Gly Leu Leu Pro Lys Pro Ser Leu Leu Ala Gln Pro Gly Pro Met
                485             490                 495

Val Ala Pro Gly Glu Asn Met Thr Leu Gln Cys Gln Gly Glu Leu Pro
            500                 505                 510

Asp Ser Thr Phe Val Leu Leu Lys Glu Gly Ala Gln Glu Pro Leu Glu
            515                 520                 525

Gln Gln Arg Pro Ser Gly Tyr Arg Ala Asp Phe Trp Met Pro Ala Val
            530                 535             540

Arg Gly Glu Asp Ser Gly Ile Tyr Ser Cys Val Tyr Tyr Leu Asp Ser
545                 550             555                 560

Thr Pro Phe Ala Ala Ser Asn His Ser Asp Ser Leu Glu Ile Trp Val
                565                 570                 575

Thr Asp Lys Pro Pro Lys Pro Ser Leu Ser Ala Trp Pro Ser Thr Met
                580             585                 590

Phe Lys Leu Gly Lys Asp Ile Thr Leu Gln Cys Arg Gly Pro Leu Pro
            595             600                 605

Gly Val Glu Phe Val Leu Glu His Asp Gly Glu Glu Ala Pro Gln Gln
            610             615                 620

Phe Ser Glu Asp Gly Asp Phe Val Ile Asn Asn Val Glu Gly Lys Gly
625                 630             635                 640

Ile Gly Asn Tyr Ser Cys Ser Tyr Arg Leu Gln Ala Tyr Pro Asp Ile
                645             650                 655

Trp Ser Glu Pro Ser Asp Pro Leu Glu Leu Val Gly Ala Ala Gly Pro
                660             665                 670

Val Ala Gln Glu Cys Thr Val Gly Asn Ile Val Arg Ser Ser Leu Ile
            675             680                 685

Val Val Val Val Val Ala Leu Gly Val Val Leu Ala Ile Glu Trp Lys
            690             695                 700

Lys Trp Pro Arg Leu Arg Thr Arg Gly Ser Glu Thr Asp Gly Arg Asp
705                 710             715                 720

Gln Thr Ile Ala Leu Glu Glu Cys Asn Gln Glu Gly Glu Pro Gly Thr
                725             730                 735

Pro Ala Asn Ser Pro Ser Ser Thr Ser Gln Arg Ile Ser Val Glu Leu
            740             745                 750

Pro Val Pro Ile
            755

<210> SEQ ID NO 20
<211> LENGTH: 784
<212> TYPE: PRT
<213> ORGANISM: Artificial Sequence
<220> FEATURE:
<223> OTHER INFORMATION: IGSF1 with leader sequence and His tag

<400> SEQUENCE: 20

Met Gly Trp Ser Tyr Ile Ile Leu Phe Leu Val Ala Thr Ala Ala Asp
1               5                   10                  15

Val His Ser Gln His His His His His His His Glu Glu Thr Glu
                20                  25                  30

Ile Val Met Pro Thr Pro Lys Pro Glu Leu Trp Ala Glu Thr Asn Phe
            35                  40                  45

Pro Leu Ala Pro Trp Lys Asn Leu Thr Leu Trp Cys Arg Ser Pro Ser
```

-continued

```
            50                  55                  60

Gly Ser Thr Lys Glu Phe Val Leu Leu Lys Asp Gly Thr Gly Trp Ile
65                  70                  75                  80

Ala Thr Arg Pro Ala Ser Glu Gln Val Arg Ala Ala Phe Pro Leu Gly
                85                  90                  95

Ala Leu Thr Gln Ser His Thr Gly Ser Tyr His Cys His Ser Trp Glu
            100                 105                 110

Glu Met Ala Val Ser Glu Pro Ser Glu Ala Leu Glu Leu Val Gly Thr
        115                 120                 125

Asp Ile Leu Pro Lys Pro Val Ile Ser Ala Ser Pro Thr Ile Arg Gly
    130                 135                 140

Gln Glu Leu Gln Leu Arg Cys Lys Gly Trp Leu Ala Gly Met Gly Phe
145                 150                 155                 160

Ala Leu Tyr Lys Glu Gly Glu Gln Glu Pro Val Gln Gln Leu Gly Ala
            165                 170                 175

Val Gly Arg Glu Ala Phe Phe Thr Ile Gln Arg Met Glu Asp Lys Asp
            180                 185                 190

Glu Gly Asn Tyr Ser Cys Arg Thr His Thr Glu Lys Arg Pro Phe Lys
        195                 200                 205

Trp Ser Glu Pro Ser Glu Pro Leu Glu Leu Val Ile Lys Glu Met Tyr
    210                 215                 220

Pro Lys Pro Phe Phe Lys Thr Trp Ala Ser Pro Val Val Thr Pro Gly
225                 230                 235                 240

Ala Arg Val Thr Phe Asn Cys Ser Thr Pro His Gln His Met Ser Phe
            245                 250                 255

Ile Leu Tyr Lys Asp Gly Ser Glu Ile Ala Ser Ser Asp Arg Ser Trp
            260                 265                 270

Ala Ser Pro Gly Ala Ser Ala Ala His Phe Leu Ile Ile Ser Val Gly
            275                 280                 285

Ile Gly Asp Gly Gly Asn Tyr Ser Cys Arg Tyr Tyr Asp Phe Ser Ile
    290                 295                 300

Trp Ser Glu Pro Ser Asp Pro Val Glu Leu Val Val Thr Glu Phe Tyr
305                 310                 315                 320

Pro Lys Pro Thr Leu Leu Ala Gln Pro Gly Pro Val Val Phe Pro Gly
            325                 330                 335

Lys Ser Val Ile Leu Arg Cys Gln Gly Thr Phe Gln Gly Met Arg Phe
            340                 345                 350

Ala Leu Leu Gln Glu Gly Ala His Val Pro Leu Gln Phe Arg Ser Val
        355                 360                 365

Ser Gly Asn Ser Ala Asp Phe Leu Leu His Thr Val Gly Ala Glu Asp
    370                 375                 380

Ser Gly Asn Tyr Ser Cys Ile Tyr Tyr Glu Thr Thr Met Ser Asn Arg
385                 390                 395                 400

Gly Ser Tyr Leu Ser Met Pro Leu Met Ile Trp Val Thr Asp Thr Phe
            405                 410                 415

Pro Lys Pro Trp Leu Phe Ala Glu Pro Ser Ser Val Val Pro Met Gly
            420                 425                 430

Gln Asn Val Thr Leu Trp Cys Arg Gly Pro Val His Gly Val Gly Tyr
        435                 440                 445

Ile Leu His Lys Glu Gly Glu Ala Thr Ser Met Gln Leu Trp Gly Ser
    450                 455                 460

Thr Ser Asn Asp Gly Ala Phe Pro Ile Thr Asn Ile Ser Gly Thr Ser
465                 470                 475                 480
```

-continued

```
Met Gly Arg Tyr Ser Cys Cys Tyr His Pro Asp Trp Thr Ser Ser Ile
                485             490             495

Lys Ile Gln Pro Ser Asn Thr Leu Glu Leu Leu Val Thr Gly Leu Leu
            500             505             510

Pro Lys Pro Ser Leu Leu Ala Gln Pro Gly Pro Met Val Ala Pro Gly
            515             520             525

Glu Asn Met Thr Leu Gln Cys Gln Gly Glu Leu Pro Asp Ser Thr Phe
        530             535             540

Val Leu Leu Lys Glu Gly Ala Gln Glu Pro Leu Glu Gln Gln Arg Pro
545             550             555             560

Ser Gly Tyr Arg Ala Asp Phe Trp Met Pro Ala Val Arg Gly Glu Asp
            565             570             575

Ser Gly Ile Tyr Ser Cys Val Tyr Tyr Leu Asp Ser Thr Pro Phe Ala
            580             585             590

Ala Ser Asn His Ser Asp Ser Leu Glu Ile Trp Val Thr Asp Lys Pro
            595             600             605

Pro Lys Pro Ser Leu Ser Ala Trp Pro Ser Thr Met Phe Lys Leu Gly
        610             615             620

Lys Asp Ile Thr Leu Gln Cys Arg Gly Pro Leu Pro Gly Val Glu Phe
625             630             635             640

Val Leu Glu His Asp Gly Glu Glu Ala Pro Gln Gln Phe Ser Glu Asp
            645             650             655

Gly Asp Phe Val Ile Asn Asn Val Glu Gly Lys Gly Ile Gly Asn Tyr
            660             665             670

Ser Cys Ser Tyr Arg Leu Gln Ala Tyr Pro Asp Ile Trp Ser Glu Pro
            675             680             685

Ser Asp Pro Leu Glu Leu Val Gly Ala Ala Gly Pro Val Ala Gln Glu
        690             695             700

Cys Thr Val Gly Asn Ile Val Arg Ser Ser Leu Ile Val Val Val Val
705             710             715             720

Val Ala Leu Gly Val Val Leu Ala Ile Glu Trp Lys Lys Trp Pro Arg
            725             730             735

Leu Arg Thr Arg Gly Ser Glu Thr Asp Gly Arg Asp Gln Thr Ile Ala
            740             745             750

Leu Glu Glu Cys Asn Gln Glu Gly Glu Pro Gly Thr Pro Ala Asn Ser
        755             760             765

Pro Ser Ser Thr Ser Gln Arg Ile Ser Val Glu Leu Pro Val Pro Ile
        770             775             780
```

```
<210> SEQ ID NO 21
<211> LENGTH: 448
<212> TYPE: PRT
<213> ORGANISM: Artificial Sequence
<220> FEATURE:
<223> OTHER INFORMATION: Heavy chain of WM-A1-3389

<400> SEQUENCE: 21

Gln Val Gln Leu Val Gln Ser Gly Ala Glu Val Lys Arg Pro Gly Ser
1               5               10              15

Ser Val Lys Val Ser Cys Lys Ala Ser Gly Gly Thr Phe Ser Thr Tyr
            20              25              30

Ala Ile Ser Trp Val Arg Gln Ala Pro Gly Gln Gly Leu Glu Trp Met
        35              40              45

Gly Arg Ile Ile Pro Phe Val Gly Thr Val Asp Tyr Ala Gln Lys Phe
    50              55              60
```

-continued

```
Gln Asp Arg Val Thr Ile Thr Ala Asp Lys Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Val Arg Asp Gly Gly Arg Ser Tyr Phe Asp Ser Trp Gly Pro Gly Ile
            100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
        210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445
```

```
<210> SEQ ID NO 22
<211> LENGTH: 217
<212> TYPE: PRT
<213> ORGANISM: Artificial Sequence
<220> FEATURE:
```

-continued

<223> OTHER INFORMATION: Light chain of WM-A1-3389

<400> SEQUENCE: 22

```
Gln Phe Val Leu Thr Gln Pro Pro Ser Val Ser Ala Ala Pro Gly Gln
1               5                   10                  15

Asp Val Ile Ile Ser Cys Ser Gly Asn Thr Ser Asn Ile Gly Ser Asn
            20                  25                  30

Leu Val Ser Trp Phe Gln Gln Phe Pro Glu Thr Ala Pro Lys Leu Leu
        35                  40                  45

Ile Tyr Asp Asn His Lys Arg Pro Ser Gly Ile Ser Asp Arg Phe Ser
    50                  55                  60

Gly Thr Lys Ser Gly Thr Ser Ala Ser Leu Ala Ile Ser Gly Leu Gln
65                  70                  75                  80

Ser Glu Asp Glu Ala Asp Tyr Tyr Cys Val Ala Trp Asp Asp Ser Leu
                85                  90                  95

Asn Gly Tyr Val Phe Gly Thr Gly Thr Lys Val Thr Val Leu Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215
```

<210> SEQ ID NO 23
<211> LENGTH: 1344
<212> TYPE: DNA
<213> ORGANISM: Artificial Sequence
<220> FEATURE:
<223> OTHER INFORMATION: Polynucleotide coding heavy chain of WM-A1-3389

<400> SEQUENCE: 23

```
caagttcagc tggttcagtc tggcgccgaa gtgaaaagac ctggcagcag cgtgaaggtg      60
tcctgcaaag cttctggcgg caccttcagc acctacgcca tctcttgggt tcgacaggcc     120
cctggacaag gcctggaatg gatgggcaga atcatcccct tgtgggcac cgtggactac      180 gcccagaaat tccaggacag agtgaccatc accgccgaca agagcaccaa caccgcctac     240
atggaactga gcagcctgag aagcgaggac accgccgtgt actactgcgt ccgagatggc     300
ggcagaagct acttcgattc ttggggccct ggcatcctgg tcacagtgtc tagcgcctct     360
acaaagggcc ccagcgtttt cccactggct cctagcagca gagcacaag cggaggaaca      420 gccgctctgg gctgtctggt caaggactac tttcccgagc ctgtgaccgt gtcttggaac     480
tctggcgctc tgacaagcgg cgtgcacaca tttccagccg tgctgcaaag cagcggcctg     540
tactctctga gcagcgtcgt gacagtgcca agcagctctc tgggcaccca gacctacatc     600
tgcaatgtga accacaagcc tagcaacacc aaggtggaca gaaaggtgga acccaagtcc     660
tgcgacaaga cccacacctg tcctccatgt cctgctccag aactgctcgg cggaccttcc     720
```

```
gtgttcctgt ttcctccaaa gcctaaggac accctgatga tcagcagaac ccctgaagtg    780
acctgcgtgg tggtggatgt gtcccacgag gacccagaag tgaagttcaa ttggtacgtg    840
gacggcgtgg aagtgcacaa cgccaagacc aagcctagag aggaacagta caactccacc    900
tacagagtgg tgtccgtgct gacagtgctg caccaggatt ggctgaacgg caaagagtac    960
aagtgcaagg tgtccaacaa ggccctgcct gctcctatcg agaaaaccat cagcaaggcc   1020
aagggccagc ctagggaacc ccaggtttac acactgcctc caagccggga agagatgaca   1080
aagaaccagg tgtccctgac ctgcctcgtg aagggcttct acccttccga tatcgccgtg   1140
gaatgggaga gcaatggcca gccagagaac aactacaaga caacccctcc tgtgctggac   1200
agcgacggct cattcttcct gtacagcaag ctgaccgtgg acaagtccag atggcagcag   1260
ggcaacgtgt tcagctgcag cgtgatgcac gaggccctgc acaaccacta cacacagaag   1320
tccctgtctc tgagccccgg caaa                                         1344

<210> SEQ ID NO 24
<211> LENGTH: 651
<212> TYPE: DNA
<213> ORGANISM: Artificial Sequence
<220> FEATURE:
<223> OTHER INFORMATION: Polynucleotide coding light chain of WM-A1-3389

<400> SEQUENCE: 24
cagtttgttc tgacacagcc tccaagcgtg tccgccgctc ctggacagga tgtgatcatc      60
agctgcagcg gcaacaccag caacatcggc agcaatctgg tgtcctggtt ccagcagttc     120
cccgagacag cccctaagct gctgatctac gacaaccaca gcggcccag cggcatcagc     180 gatagattca gcggcacaaa gagcggcacc agcgcttctc tggccatctc tggactgcag     240
agcgaggacg aggccgacta ctattgtgtg gcctgggacg acagcctgaa cggctatgtg     300
tttggcaccg gcaccaaagt gaccgtgctg agaacagtgg ccgctcctag cgtgttcatc     360
ttcccacctt ccgacgagca gctgaagtct ggcacagcca gcgttgtgtg cctgctgaac     420
aacttctacc ctcgggaagc caaggtgcag tggaaggtgg acaatgccct gcagtccggc     480
aacagccaag agagcgtgac agagcaggac agcaaggact ccacctacag cctgagcagc     540
accctgacac tgagcaaggc cgattacgag aagcacaagg tgtacgcctg cgaagtgaca     600
caccagggcc tgtctagccc tgtgaccaag agcttcaaca gaggcgagtg c             651
```

ANTI-IGSF1 ANTIBODY AND USE THEREOF

REFERENCE TO AN ELECTRONIC SEQUENCE LISTING

The contents of the electronic sequence listing (950153_401USPC_SequenceListing. TXT; Size: 29,497 bytes; and Date of Creation: Sep. 14, 2022) is herein incorporated by reference in its entirety.

TECHNICAL FIELD

The present invention relates to a novel antibody that specifically binds to IGSF1 and a pharmaceutical composition for preventing or treating cancer, comprising the same as an active ingredient.

BACKGROUND ART

Although research on cancer has been conducted in depth for a long time, the incidence of cancer continues to increase due to environmental pollution and bad eating habits. More than 100 million cancer patients occur worldwide every year, and the World Health Organization (WHO) ranks cancer as one of the leading causes of death. As such, cancer is a major disease that occupies the first place in mortality in modern society, and there is no epoch-making treatment despite many studies to date.

In the treatment of cancer, chemotherapies such as anti-cancer agents are effective to some extent, but many studies are required due to various pathogenesis of cancer and resistance to anticancer agents. Although the cancer treatment rate has improved due to the development of diagnosis and treatment techniques in recent decades, the 5-year survival rate for many advanced cancers remains in the range of 5 to 50%. In addition, in some cancers, despite various studies and treatments, the survival rate over the past 20 years has not changed significantly.

As such, cancer is not easily treated by conventional cancer treatment regimens, relapses, and metastases to other sites occur, so a more essential treatment method is required. Accordingly, there is growing interest in developing substances for treating cancer by targeting biomarkers that are characteristic of cancer cells that are determined to be the cause of malignancy, metastasis, and recurrence of cancer.

On the other hand, Korean Patent Application Publication No. 2016-0014564 discloses that the IGSF1 (immunoglobulin superfamily member 1) gene may be used as a biomarker for predicting sensitivity to MET (mesenchymal-epithelial transition factor) inhibitors. In the above literature, it is disclosed that an anticancer agent having a high therapeutic effect may be selected by determining the sensitivity of each patient using the biomarker before treating a patient with cancer. However, it has not been disclosed that an antibody specific for IGSF1 may be utilized as an anticancer agent.

DETAILED DESCRIPTION OF INVENTION

Technical Problem

The present inventors have studied to develop an anti-cancer agent having a high therapeutic effect, in particular, a therapeutic agent for effectively treating a cancer in which IGSF1 is overexpressed. As a result, the present inventors have developed an antibody that specifically binds to the C-terminus of IGSF1, and found that the antibody effectively prevents or treats cancer.

Solution to Problem

In order to achieve the above object, in one aspect of the present invention, there is provided an anticancer agent comprising an anti-IGSF1 antibody that specifically binds to the C-terminus of IGSF1 as an active ingredient.

In another aspect of the present invention, there is provided an antibody specific for IGSF1 or a fragment thereof, comprising a heavy chain variable region comprising H-CDR1 of SEQ ID NO: 1, H-CDR2 of SEQ ID NO: 2 and H-CDR3 of SEQ ID NO: 3; and a light chain variable region comprising L-CDR1 of SEQ ID NO: 4, L-CDR2 of SEQ ID NO: 5 and L-CDR3 of SEQ ID NO: 6.

In another aspect of the present invention, there is provided a polynucleotide encoding the antibody specific for IGSF1 or fragment thereof, an expression vector comprising the polynucleotide, and a transformed cell into which the expression vector is introduced.

In another aspect of the present invention, there is provided a method of producing an antibody specific for IGSF1 or a fragment thereof, comprising culturing the transformed cell; and recovering an anti-IGSF1 antibody or a fragment thereof.

In another aspect of the present invention, there is provided a pharmaceutical composition for preventing or treating cancer, comprising the antibody specific for IGSF1 or fragment thereof as an active ingredient.

In another aspect of the present invention, there is provided a method for preventing or treating cancer, comprising administering to a subject the antibody specific for IGSF1 or fragment thereof.

Effects of Invention

The anti-IGSF1 antibody according to the present invention exhibited high specificity and high binding capacity to IGSF1. The anti-IGSF1 antibody according to the present invention increased the infiltration of immune cells in the spheroids when lung cancer cell spheroids in which IGSF1 is overexpressed were co-cultured with human peripheral mononuclear cells. In addition, the anti-IGSF1 antibody according to the present invention inhibited tumor growth in a humanized mouse transplanted with human lung cancer cells in which IGSF1 is overexpressed. In addition, the antibody increased the expression of cytokines in cytotoxic T lymphocytes present in tumor tissues. Through the above results, it was confirmed that the anti-IGSF1 antibody may inhibit tumor growth by increasing the infiltration of immune cells into tumor tissues in which the IGSF1 expression is increased and immune response. Therefore, the anti-IGSF1 antibody may be utilized as an anticancer agent for effectively treating cancer in which IGSF1 is overexpressed.

US 12,630,629 B2

3

IGSF1 O/E) and the control (NCI-H292 MOCK) spheroids were co-cultured with human peripheral mononuclear cells (PBMC).

Figure 3:
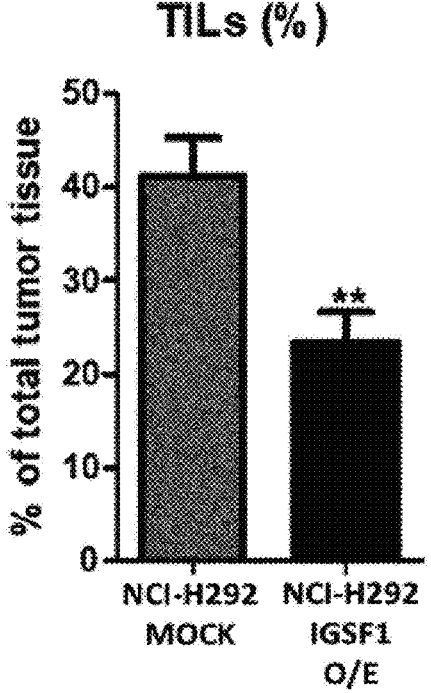

FIG. 3 is a graph showing a result obtained by analyzing through flow cytometry the distribution degree of hCD45+ cells in order to confirm the presence of tumor-infiltrating lymphocytes in the tumor tissues of mice transplanted with IGSF1 overexpressing human lung cancer cells (NCI-H292 IGSF1 O/E) or the control (NCI-H292 MOCK).

Figure 4:
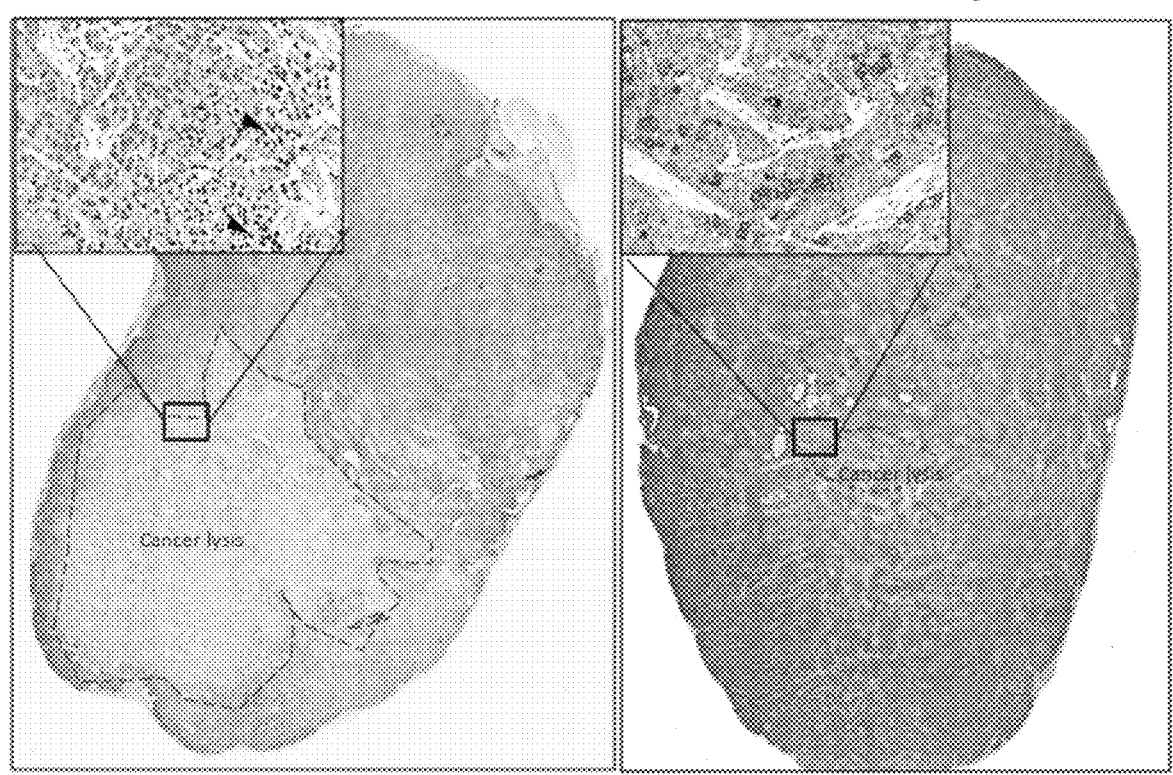

FIG. 4 illustrates a result obtained by confirming by immunohistochemistry staining method the expression of IGSF1 and the presence of tumor-infiltrating lymphocytes in the tumor tissues of mice transplanted with IGSF1 overexpressing human lung cancer cells (NCI-H292 IGSF1 O/E) or the control (NCI-H292 MOCK).

Figure 5:
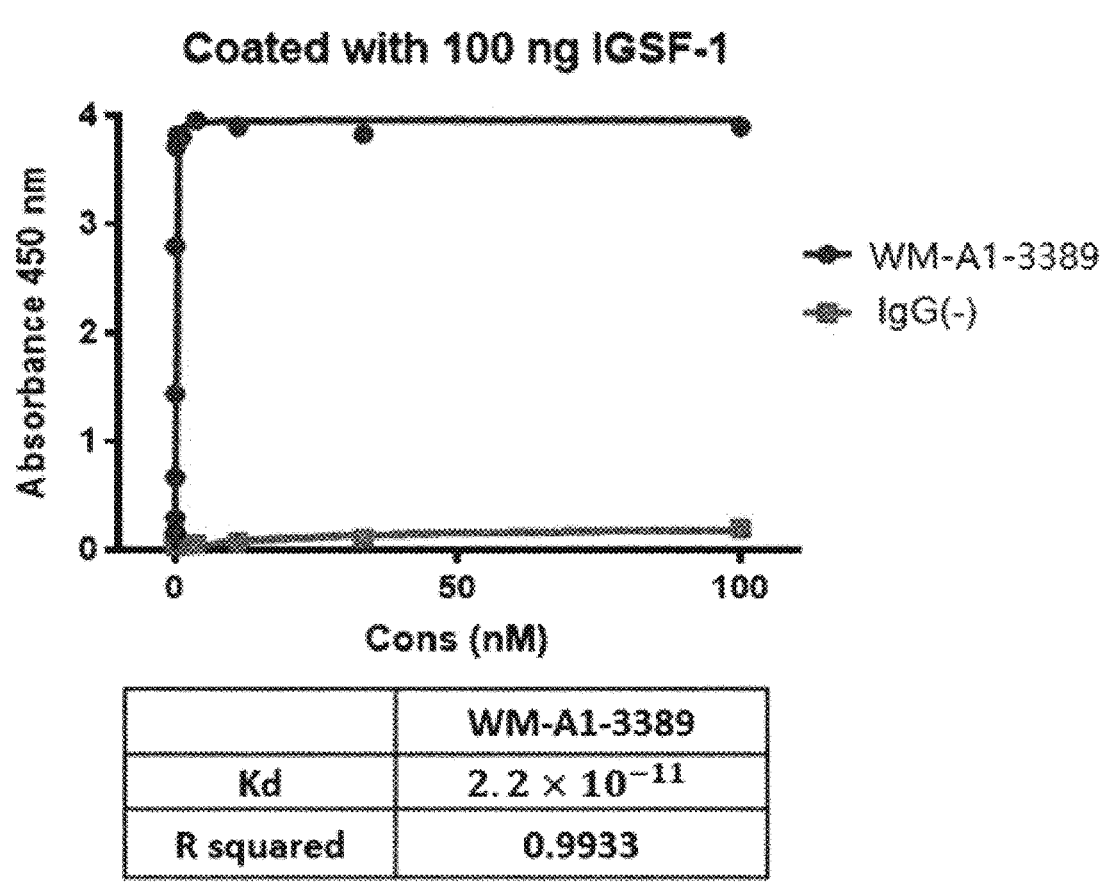

FIG. 5 is a graph showing a result obtained by analyzing the binding affinity of the WM-A1-3389 antibody to the IGSF1 antigen using ELISA.

Figure 6:
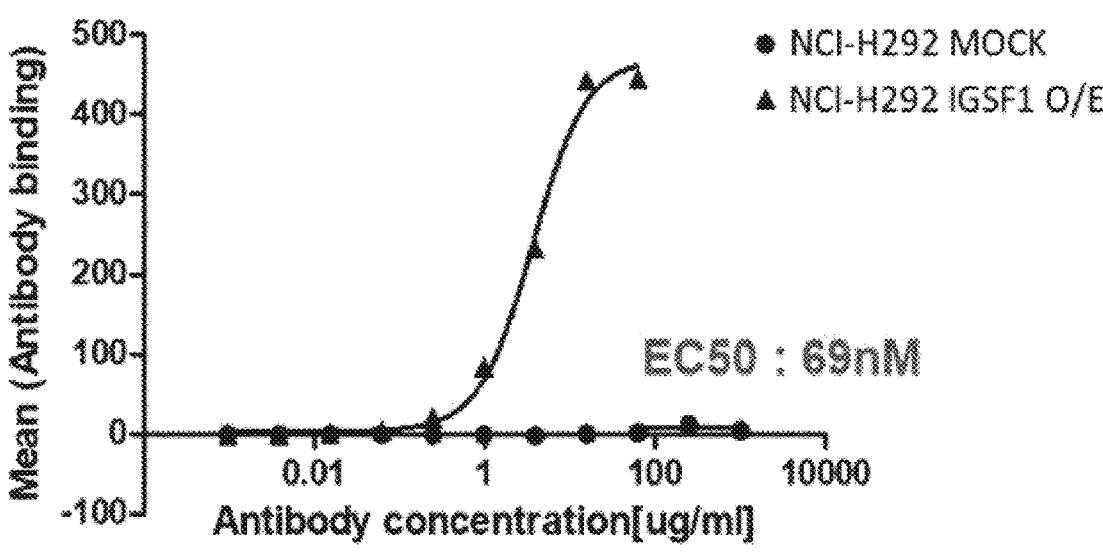

FIG. 6 is a graph showing a result obtained by analyzing the binding affinity of the WM-A1-3389 antibody to the IGSF1 antigen in cells using FACS analysis.

Figure 7:
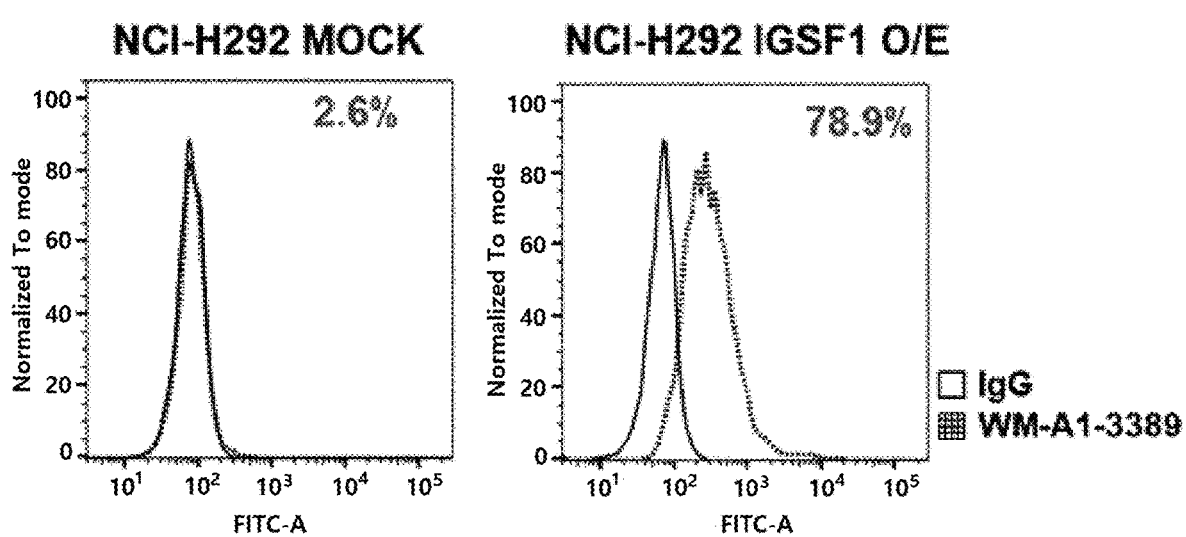

FIG. 7 is a graph showing a result obtained by analyzing the binding capacity of the WM-A1-3389 antibody to IGSF1 expressed in cells in IGSF overexpressing human lung cancer cells (NCI-H292 IGSF1 O/E) and the control (NCI-H292 MOCK) using FACS analysis.

Figure 8:
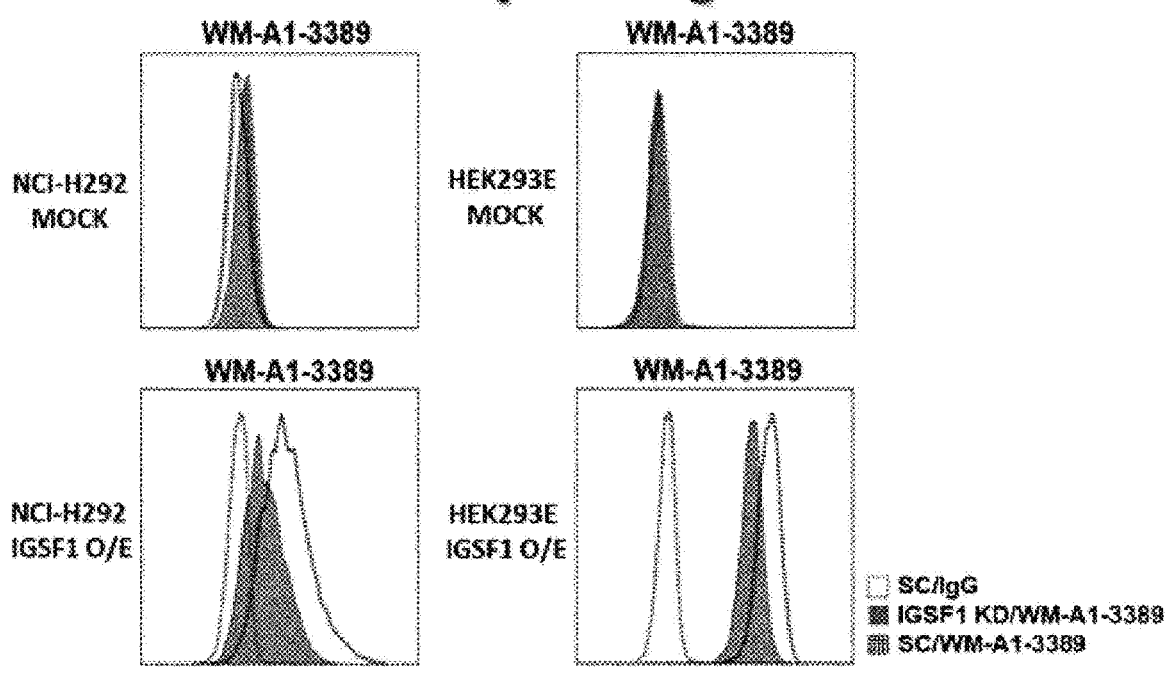

FIG. 8 is a graph showing a result obtained by analyzing the binding specificity of the WM-A1-3389 antibody in IGSF1 knock-down (K/D) cell line treated with shIGSF1 in two IGSF1 overexpressing human lung cancer cells (NCI-H292 IGSF1 O/E and HEK293E IGSF1 O/E) and the control (NCI-H292 MOCK and HEK293E MOCK).

Figure 9:
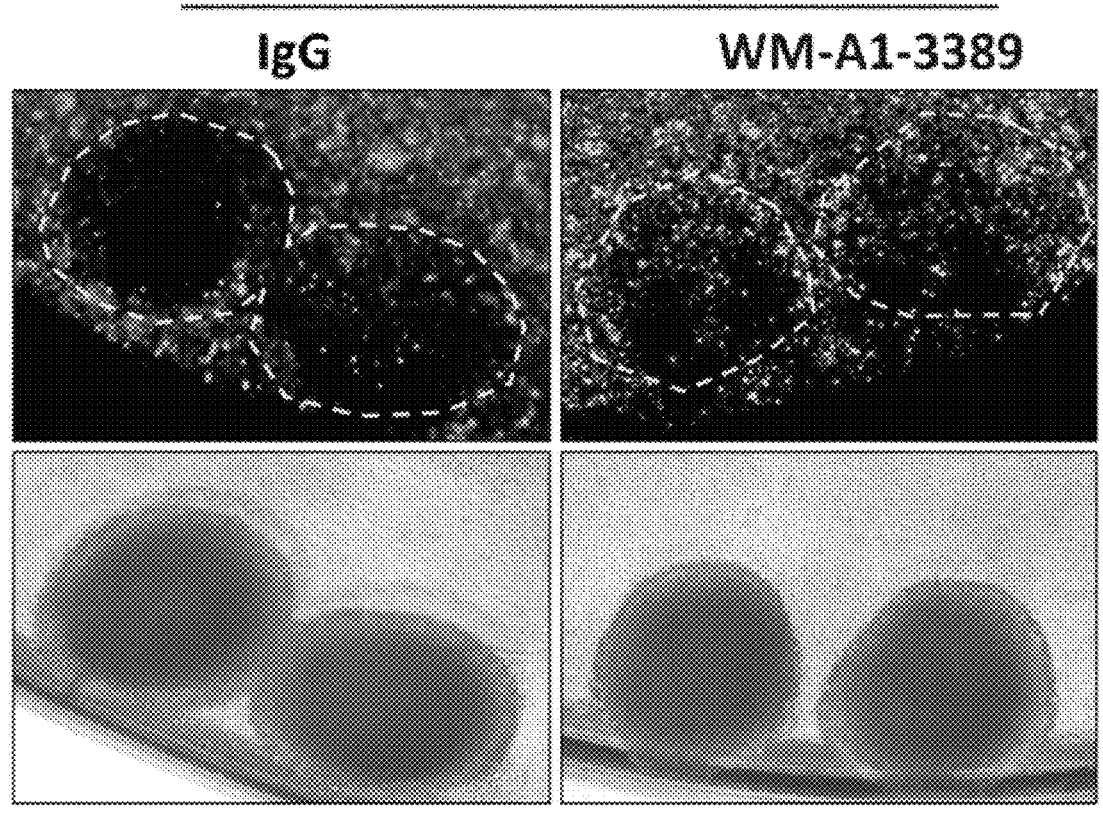

FIG. 9 illustrates a result obtained by confirming through a microscope image tumor-infiltrating lymphocytes (TIL) present in the spheroids after treatment with IgG or the WM-A1-3389 antibody when IGSF1 overexpressing human lung cancer cell (NCI-H292 IGSF1 O/E) spheroids were co-cultured with human peripheral mononuclear cells (PBMC).

Figure 10:
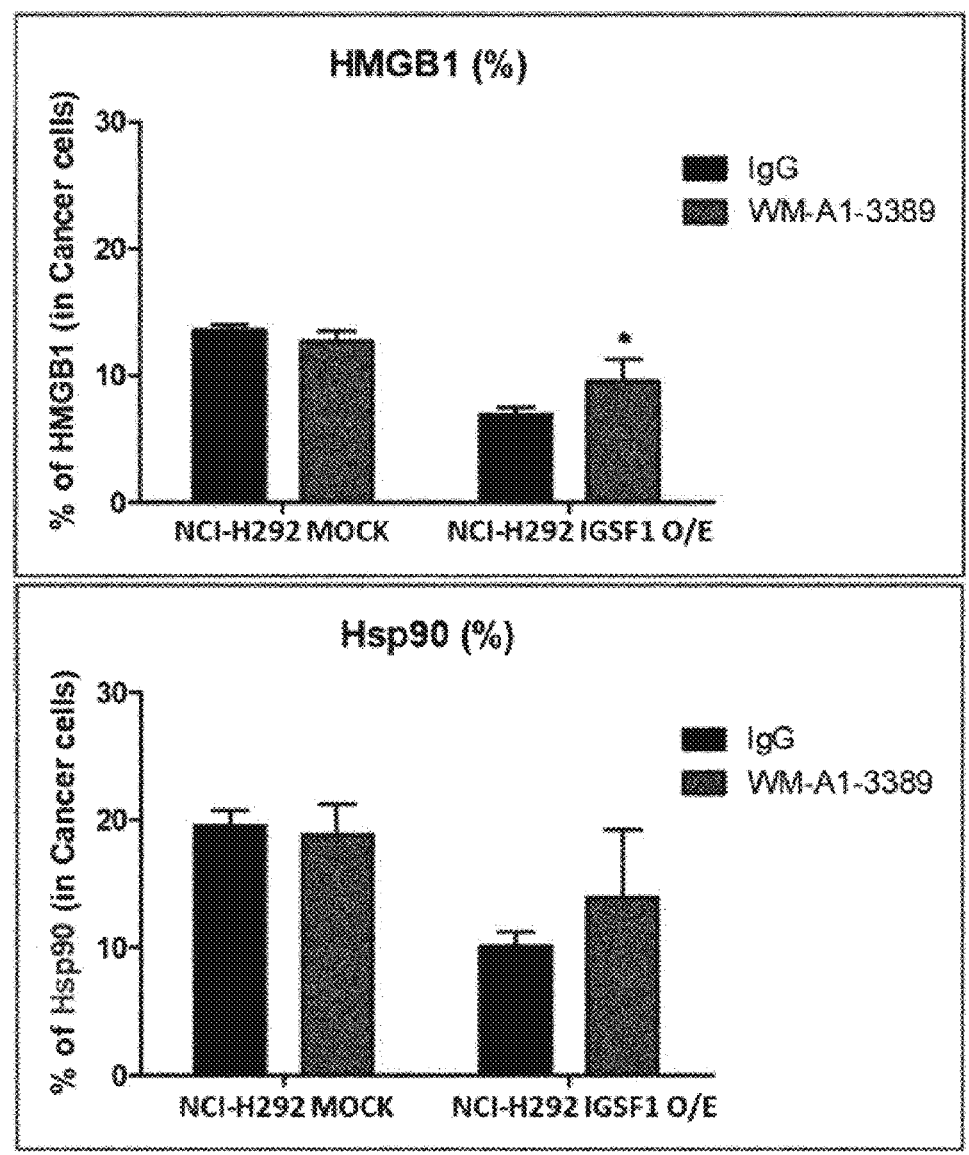

FIG. 10 is a graph showing the expression of HMGB1 and Hsp90 in the spheroids after treatment with IgG or the WM-A1-3389 antibody when IGSF1 overexpressing human lung cancer cells (NCI-H292 IGSF1 O/E) and the control (NCI-H292 MOCK) spheroids were co-cultured with human peripheral mononuclear cells (PBMC).

Figure 11:
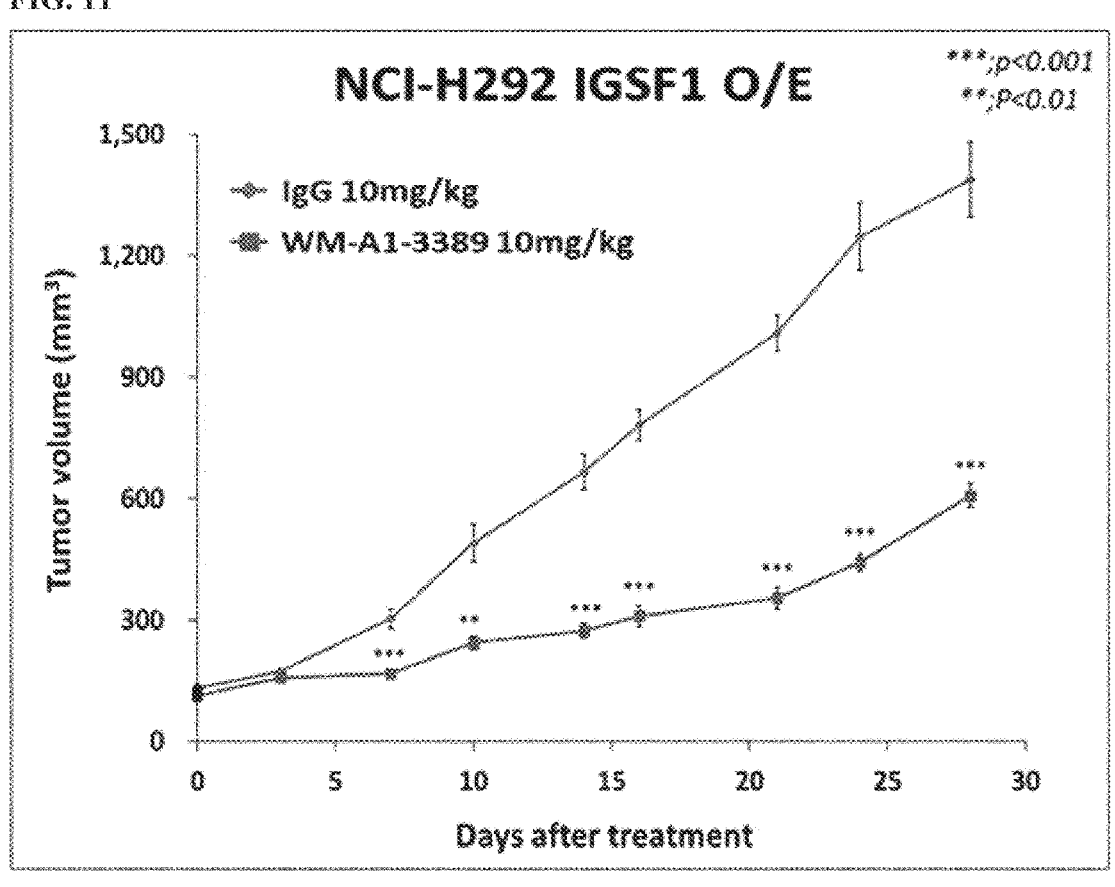

FIG. 11 is a graph showing a result obtained by measuring the tumor size of a group administered with IgG or the WM-A1-3389 antibody in a mouse model transplanted with IGSF1 overexpressing human lung cancer cells (NCI-H292 IGSF1 O/E).

Figure 12:
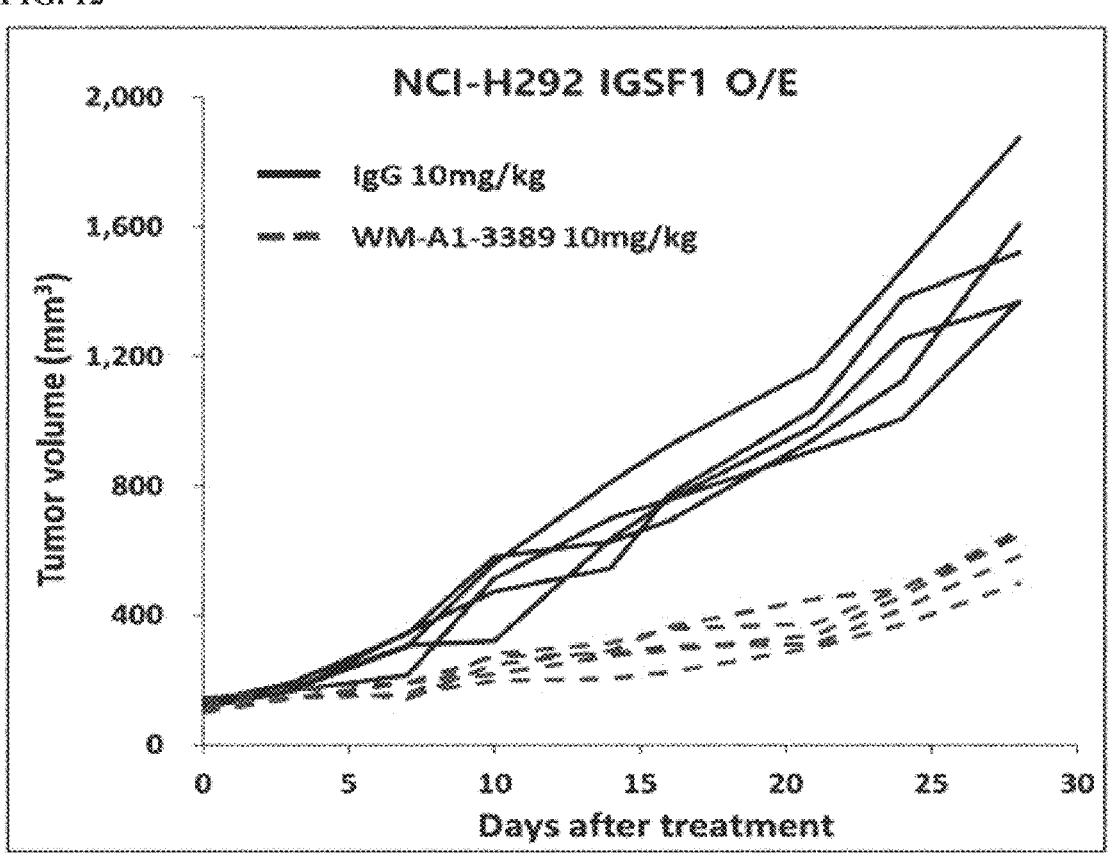

FIG. 12 is a graph showing the tumor size of a mouse group administered with IgG or the WM-A1-3389 antibody by a subject in a mouse model transplanted with IGSF1 overexpressing human lung cancer cells (NCI-H292 IGSF1 O/E).

Figure 13:
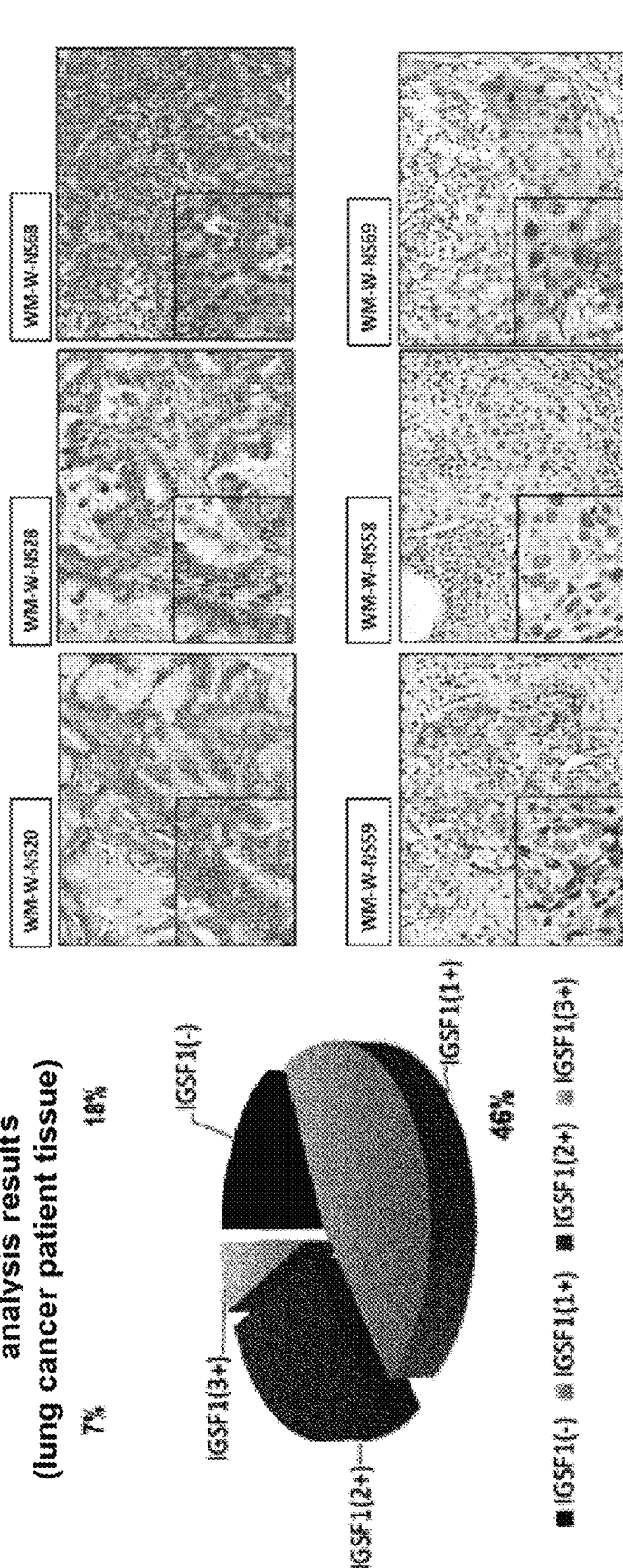

FIG. 13 illustrates a result obtained by analyzing the expression level of IGSF1 in Caucasian lung cancer patient tissue.

BEST MODE FOR CARRYING OUT THE INVENTION

In one aspect of the present invention, there is provided an anticancer agent comprising an anti-IGSF1 antibody that specifically binds to the C-terminus of IGSF1 as an active ingredient.

As used herein, the term "IGSF1" is a membrane protein encoded by the IGSF1 gene found on the X chromosome of humans and other mammalian species. Although the function of IGSF1 in normal cells is not well known, IGSF1 mutation is known to cause diseases such as IGSF1 deficiency syndrome or central hypothyroidism.

In the present invention, the IGSF1 may be included without limitation as long as it is mammalian IGSF1, but preferably, it may refer to human IGSF1. In addition, in the present invention, the IGSF1 protein includes all of the native IGSF1 protein or or variants thereof, but is not limited thereto. The native IGSF1 protein generally refers to a polypeptide comprising the amino acid sequence of the native IGSF1 protein, and the amino acid sequence of the native IGSF1 protein generally refers to an amino acid sequence found in a naturally occurring IGSF1. The information on the IGSF1 may be obtained from a known database such as GenBank of the National Institutes of Health of the United States of America, and for example, may have the amino acid sequence of Genebank accession number NP_001164433.1 or the amino acid sequence of SEQ ID NO: 19, but is not limited thereto.

As used herein, the term "anti-IGSF1 antibody" refers to an antibody capable of binding to IGSF1, and may be used interchangeably with an "antibody specific for IGSF1" in the present invention. In particular, the anti-IGSF1 antibody may specifically bind to the C-terminus of IGSF1. The form of the antibody may include both a whole antibody and an antibody fragment thereof. 5 As used herein, the term "anticancer agent" may include any composition or medicament that exhibits a preventive or therapeutic effect on cancer.

In the present invention, the anti-IGSF1 antibody that binds to the C-terminus of IGSF1 may effectively kill cancer in which IGSF1 is overexpressed. In this case, the cancer may be any one selected from the group consisting of gastric cancer, liver cancer, lung cancer, non-small cell lung cancer, colorectal cancer, bladder cancer, bone cancer, blood cancer, breast cancer, melanoma, thyroid cancer, parathyroid cancer, bone marrow cancer, rectal cancer, throat cancer, laryngeal cancer, esophageal cancer, pancreatic cancer, tongue cancer, skin cancer, brain tumor, uterine cancer, head or neck cancer, gallbladder cancer, oral cancer, perianal cancer, colon cancer, and central nervous system tumor, but is not limited thereto as long as it is a cancer in which IGSF1 is overexpressed.

Anti-IGSF1 Antibody

In another aspect of the present invention, there is provided an antibody specific for IGSF1 or a fragment thereof, comprising a heavy chain variable region comprising H-CDR1 of SEQ ID NO: 1, H-CDR2 of SEQ ID NO: 2 and H-CDR3 of SEQ ID NO: 3; and a light chain variable region comprising L-CDR1 of SEQ ID NO: 4, L-CDR2 of SEQ ID NO: 5 and L-CDR3 of SEQ ID NO: 6.

As used herein, the term "antibody" refers to an immunoglobulin molecule that immunologically reacts with a specific antigen, and refers to a protein molecule that specifically recognizes an antigen. The antibody includes a whole antibody, a monoclonal antibody, a polyclonal antibody, a single domain antibody, a single chain antibody, a multispecific antibody, a human antibody, a humanized antibody, a chimeric antibody, an intrabody, scFv, an Fab fragment, an F(ab') fragment, Fv (sdFv) linked by disulfide bonds and an epitope binding fragment of any of the above, but is not limited thereto.

The heavy and light chains of an immunoglobulin may include a constant region and a variable region, respectively.

The light and heavy chain variable regions of an immunoglobulin include three variable regions called complementarity determining regions (CDRs) and four framework regions (FRs). The CDRs mainly serve to bind to an epitope of an antigen. The CDRs of each chain are typically called CDR1, CDR2, and CDR3 sequentially, starting from the N terminus, and are identified by the chain in which a specific CDR is located. The antibody specific for IGSF1 and fragment thereof of the present invention may comprise a heavy chain variable region (VH) comprising H-CDR1 of SEQ ID NO: 1, H-CDR2 of SEQ ID NO: 2 and H-CDR3 of SEQ ID NO: 3. In addition, the antibody specific for IGSF1 and fragment thereof of the present invention may comprise a light chain variable region (VL) comprising L-CDR1 of SEQ ID NO: 4, L-CDR2 of SEQ ID NO: 5 and L-CDR3 of SEQ ID NO: 6. In this case, the heavy chain variable region may have the amino acid sequence of SEQ ID NO: 7, and the light chain variable region may have the amino acid sequence of SEQ ID NO: 8. The antibody herein may be referred to as WM-A1-3389.

The heavy chain variable region of the antibody may comprise or consist of an amino acid sequence having about 90%, about 91%, about 92%, about 93%, about 94%, about 95%, about 96%, about 97%, about 98%, about 99%, or about 100% identity to the amino acid sequence of SEQ ID NO: 7. In addition, the light chain variable region of the antibody may comprise or consist of an amino acid sequence having about 90%, about 91%, about 92%, about 93%, about 94%, about 95%, about 96%, about 97%, about 98%, about 99% or about 100% identity to the amino acid sequence of SEQ ID NO: 8.

The heavy chain constant region (CH) of an immunoglobulin exhibits different amino acid compositions and sequences and thus possess different types of antigenicity. Therefore, immunoglobulins may be classified into five categories and may be referred to as immunoglobulin isotypes, i.e., IgM, IgD, IgG, IgA and IgE. The corresponding heavy chains are the μ chain, the δ chain, the γ chain, the α chain and the δ chain, respectively. In addition, depending on the amino acid composition of the hinge region and the number and position of heavy chain disulfide bonds, the same type of Ig may be classified into different subtypes. For example, IgG may be classified into IgG1, IgG2, IgG3 and IgG4. Light chains may be classified into a κ or λ chain according to different constant regions. Each of the five types of IgG may have either a κ or a λ chain.

When the antibody specific for IGSF1 of the present invention includes a constant region, it may include a constant region that is derived from IgG, IgA, IgD, IgE, IgM, or a partial hybrid thereof.

As used herein, the term "hybrid" refers to the presence of sequences corresponding to immunoglobulin heavy chain constant regions having two or more different origins within a single chain immunoglobulin heavy chain constant region. For example, hybridization of domains consisting of 1 to 4 domains selected from the group consisting of CH1, CH2 and CH3 of IgG, IgA, IgD, IgE and IgM is possible.

In addition, when the antibody specific for IGSF1 of the present invention comprises a light chain constant region (LC), the light chain constant region may be derived from a λ or κ light chain.

As used herein, the term "fragment of antibody" refers to an Fab fragment, an Fab' fragment, an F(ab')₂ fragment having antigen-binding activity, as well as an scFv fragment which is Fv fragment that binds to IGSF1, and includes CDR regions of the antibodies described in the present invention. The Fv fragment is the smallest fragment of antibody, comprising a heavy chain variable region and a light chain variable region, without constant regions, and possessing all antigen-binding sites.

Polynucleotide Encoding Anti-IGSF1 Antibody

In another aspect of the present invention, there is provided a polynucleotide encoding an antibody specific for IGSF1 or a fragment thereof. The anti-IGSF1 antibody and fragment thereof are as described above. In this case, the heavy chain region of the polynucleotide may comprise the nucleotide sequence of SEQ ID NO: 9, and the light chain region may comprise the nucleotide sequence of SEQ ID NO: 10.

If the polynucleotide encodes the same polypeptide, one or more bases may be mutated by substitution, deletion, insertion or a combination thereof. When the polynucleotide sequence is prepared by chemical synthesis, synthesis methods well known in the art, for example, the method described in the literature (Engels and Uhlmann, Angew Chem IntEd Engl., 37:73-127, 1988) may be used, and may include triester, phosphite, phosphoramidite and H-phosphate methods, PCR and other auto-primer methods, synthesis methods of oligonucleotide on a solid support, and the like.

According to one embodiment, the polynucleotide may comprise a nucleotide sequence having at least about 70%, at least about 75%, at least about 80%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99% or at least about 100% identity to the nucleotide sequence of SEQ ID NO: 9 or SEQ ID NO: 10, respectively.

The polynucleotide may further comprise a signal sequence or a leader sequence. As used herein, the term "signal sequence" refers to a nucleic acid encoding a signal peptide that directs secretion of a target protein. The signal peptide is translated and then cleaved in a host cell. Specifically, the signal sequence of the present invention is nucleotides encoding an amino acid sequence that initiates the transports of a protein across the ER (endoplasmic reticulum) membrane.

Signal sequences are well known in the art for their characteristics. Such signal sequences typically contain 16 to 30 amino acid residues, and may contain more or fewer amino acid residues than such amino acid residues. A conventional signal peptide is composed of three regions, that is, a basic N-terminal region, a central hydrophobic region, and a more polar C-terminal region. The central hydrophobic region contains 4 to 12 hydrophobic residues that cause the signal sequence to be immobilized during transports of an immature polypeptide through the membrane lipid bilayer.

After initiation, the signal sequence is cleaved in the lumen of the ER by intracellular enzymes, commonly known as signal peptidases. In this case, the signal sequence may be a secretory signal sequence of tPa (tissue plasminogen activation), HSV gDs (signal sequence of herpes simplex virus glycoprotein D), an IgG signal sequence or a growth hormone. Preferably, a secretory signal sequence used in higher eukaryotic cells including mammals and the like may be used.

The signal sequence useful in the present invention includes antibody light chain signal sequences, such as antibody 14.18 (Gillies et al., J. Immunol. Methods, 1989. 125:191-202), antibody heavy chain signal sequences, such as MOPC141 antibody heavy chain signal sequence (Sakano et al., Nature, 1980. 286:676-683) and other signal sequences known in the art (see, e.g., Watson et al., Nucleic Acid Research, 1984. 12:5145-5164).

Vector Loaded with Polynucleotide

In another aspect of the present invention, there is provided a vector comprising a polynucleotide encoding the antibody specific for IGSF1 or fragment thereof. The heavy chain region of the polynucleotide may comprise the nucleotide sequence of SEQ ID NO: 9, and the light chain region may comprise the nucleotide sequence of SEQ ID NO: 10. In addition, the polynucleotide may further comprise a signal sequence or a leader sequence. Herein, an antibody specific for IGSF1 and a fragment thereof, and a signal sequence are as described above.

In this case, the vector may be two vectors containing the polynucleotides of the heavy chain and the light chain, respectively, or a bicistronic vector containing both the polynucleotides.

As used herein, the term "vector" may be introduced into a host cell to be recombined with and inserted into the genome of the host cell. Alternatively, the vector is understood as nucleic acid means containing a nucleotide sequence which is spontaneously replicable as an episome. The vectors include linear nucleic acids, plasmids, phagemids, cosmids, RNA vectors, viral vectors, mini-chromosomes, and analogs thereof. Examples of the viral vector include retroviruses, adenoviruses, and adeno-associated viruses, but are not limited thereto.

Specifically, the vector may include plasmid DNA, phage DNA, and the like; and commercially developed plasmids (pUC18, pBAD, pIDTSAMRT-AMP, and the like), *E. coli*-derived plasmids (pYG601BR322, pBR325, pUC118, pUC119, and the like), *Bacillus subtilis*-derived plasmids (pUB110, pTP5, and the like), yeast-derived plasmids (YEp13, YEp24, YCp50, and the like), phage DNA (Charon4A, Charon21A, EMBL3, EMBL4, λgt10, λgt11, λZAP, and the like), animal viral vectors (retroviruses, adenoviruses, vaccinia viruses, and the like), insect viral vectors (baculoviruses and the like) and the like. Since the vector exhibits different expression levels and modification and the like of a protein depending on a host cell, it is preferred to select and use a host cell which is most suitable for the purpose.

In addition, the plasmid may contain a selectable marker such as an antibiotic resistance gene, and host cells retaining the plasmid may be cultured under selective conditions.

As used herein, the term "gene expression" or "expression" of a target protein is understood to mean transcription of DNA sequences, translation of mRNA transcripts, and secretion of fusion protein products or fragments thereof. A useful expression vector may be RcCMV (Invitrogen, Carlsbad) or a variant thereof. The expression vector may contain a human cytomegalovirus (CMV) promoter for promoting continuous transcription of a target gene in mammalian cells, and a bovine growth hormone polyadenylation signal sequence for increasing the stability level of RNA after transcription.

Transformed Cell Expressing Anti-IGSF1 Antibody

In another aspect of the present invention, there is provided a transformed cell into which an expression vector comprising a polynucleotide encoding the antibody specific for IGSF1 or fragment thereof is introduced. The antibody specific for IGSF1 and fragment thereof are as described above.

As used herein, the term "transformed cell" refers to a prokaryotic cell and a eukaryotic cell into which a recombinant expression vector may be introduced. The transformed cell may be constructed by introducing a vector into a host cell and transforming it. In addition, the fusion protein of the present invention may be produced by expressing the polynucleotide included in the vector.

The transformation may be performed by various methods. As long as it may produce the fusion protein of the present invention, it is not particularly limited thereto. Specifically, the transformation method, for example, CaCl$_2$) precipitation method, Hanahan method whose efficiency has been increased by using a reducing agent such as dimethyl sulfoxide (DMSO) in CaCl$_2$) precipitation method, electroporation, calcium phosphate precipitation method, protoplast fusion method, agitation method using silicon carbide fiber, *agrobacterium* mediated transformation method, transformation method using PEG, dextran sulfate, lipofectamine and dry/inhibition mediated transformation method, and the like may be used. In addition, by using the infection as a means, a target object may be delivered into a cell using virus particles. In addition, a vector may be introduced into a host cell by gene bombardment or the like.

In addition, as long as the host cell used for the construction of the transformed cell may also produce the fusion protein of the present invention, it is not particularly limited thereto. Specifically, the host cell may include, but is not limited to, prokaryotic cells, eukaryotic cells, and cells of mammalian, plant, insect, fungal, or bacterial origin. As an example of the prokaryotic cells, *E. coli* may be used. In addition, as an example of the eukaryotic cells, yeast may be used. In addition, for the mammalian cells, CHO cells, F2N cells, COS cells, BHK cells, Bowes melanoma cells, HeLa cells, 911 cells, AT1080 cells, A549 cells, SP2/0 cells, human lymphoblastoids, NSO cells, HT-1080 cells, PERC.6 cells, HEK293 cells, HEK293T cells or the like may be used, but are not limited thereto. Any cells which are known to those of ordinary skill in the art to be usable as mammalian host cells may be used.

As described above, for optimization of properties of an anti-IGSF1 antibody and a fragment thereof as a therapeutic agent or for any other purpose, glycosylation pattern (for example, sialic acid, fucosylation, glycosylation) of the fusion protein may be adjusted by manipulating glycosylation-related genes possessed by host cells through methods known to those of ordinary skill in the art.

Method of Producing Anti-IGSF1 Antibody

In another aspect of the present invention, there is provided a method of producing the antibody specific for IGSF1 or fragment thereof. In this case, the antibody specific for IGSF 1 and fragment thereof are as described above.

A method of producing the fusion protein may comprise i) culturing the transformed cell; and ii) recovering the anti-IGSF1 antibody or fragment thereof of the present invention.

As used herein, the term "culture" refers to a method of growing microorganisms in an appropriately artificially controlled environmental condition.

A method of culturing the transformed cell may be carried out using methods well known in the art. Specifically, the culture is not particularly limited as long as it may be produced by expressing the fusion protein of the present invention. Specifically, the culture may be carried out in a batch process, or carried out continuously in a fed batch or repeated fed batch process.

In addition, recovering the fusion protein dimer from the culture may be performed by methods known in the art. Specifically, the recovery method is not particularly limited as long as it may recover the produced fusion protein of the present invention. Preferably, the recovery method may be methods such as centrifugation, filtration, extraction, spraying, drying, evaporation, precipitation, crystallization, electrophoresis, fractional dissolution (for example, ammonium sulfate precipitation), chromatography (for example, ion exchange, affinity, hydrophobicity, and size exclusion) and the like.

Use of Anti-IGSF1 Antibody

In another aspect of the present invention, there is provided a pharmaceutical composition for preventing or treating cancer, comprising the IGSF1 antibody or fragment thereof as an active ingredient.

In this case, the cancer may be a cancer in which IGSF1 is overexpressed. In addition, the cancer may be any one selected from the group consisting of gastric cancer, liver cancer, lung cancer, non-small cell lung cancer, colorectal cancer, bladder cancer, bone cancer, blood cancer, breast cancer, melanoma, thyroid cancer, parathyroid cancer, bone marrow cancer, rectal cancer, throat cancer, laryngeal cancer, esophageal cancer, pancreatic cancer, tongue cancer, skin cancer, brain tumor, uterine cancer, head or neck cancer, gallbladder cancer, oral cancer, perianal cancer, colon cancer, and central nervous system tumor.

The term "prevention" refers to any action that inhibits the occurrence of cancer or delays the onset of cancer by administration of the pharmaceutical composition. The term "treatment" refers to any action that improves or beneficially changes the symptoms of cancer by administration of the pharmaceutical composition.

In the pharmaceutical composition for the prevention or treatment of cancer of the present invention, the anti-IGSF1 antibody or fragment thereof may be included in any amount (effective amount) depending on the use, formulation, purpose of combining, and the like, as long as it may exhibit an anticancer activity. Herein, "effective amount" refers to an amount of an active ingredient capable of inducing an anticancer effect. Such an effective amount may be determined experimentally within the ordinary ability of those of ordinary skill in the art. The pharmaceutical composition of the present invention may comprise the antibody as an active ingredient in an amount of from about 0.1% by weight to about 90% by weight, specifically from about 0.5% by weight to about 75% by weight, more specifically from about 1% by weight to about 50% by weight based on the total weight of the composition.

The pharmaceutical composition of the present invention may comprise a conventional, non-toxic pharmaceutically acceptable carrier to be combined into a formulation according to a conventional method.

The pharmaceutically acceptable carrier may be any non-toxic material suitable for delivery to a patient. Distilled water, alcohol, fats, waxes and inert solids may be included as a carrier. In addition, a pharmaceutically acceptable adjuvant (buffering agent, dispersing agent) may be included in the pharmaceutical composition.

As used herein, the term "pharmaceutically acceptable carrier" refers to a carrier or diluent that does not irritate the organism and does not inhibit the biological activity and property of the administered compound. Pharmaceutically acceptable carriers for compositions formulated as liquid solutions are sterile and biocompatible, and saline, sterile water, Ringer's solution, buffered saline, albumin injection solution, dextrose solution, maltodextrin solution, glycerol, ethanol, and a mixture of one or more components of these components may be used, and other conventional additives such as sweeteners, solubilizers, wetting agents, emulsifiers, isotonic agents, absorbents, antioxidants, preservatives, lubricants, fillers, buffers, and bacteriostats may be added as needed.

The composition of the present invention may be prepared in a variety of formulations for parenteral administration (such as, intramuscular, intravenous or subcutaneous injection). When the pharmaceutical composition of the present invention is prepared as a parenteral formulation, it may be formulated in the form of injections, transdermal preparations, nasal inhalants and suppositories together with a suitable carrier according to methods known in the art. Preparations for injection include sterile aqueous solutions, non-aqueous solutions, suspensions, emulsions, freeze-dried preparations and suppositories. Non-aqueous solvents and suspending agents include propylene glycol, polyethylene glycol, vegetable oils such as olive oil, and injectable esters such as ethyl oleate. As the base of the suppositories, WITEPSOL® suppository base, Macrogol, Tween 61, cacao butter, laurin, glycerogelatin, and the like may be used. On the other hand, injections may include conventional additives such as solubilizers, isotonic agents, suspending agents, emulsifiers, stabilizers, and preservatives.

Formulation of a pharmaceutical composition is known in the art, and specifically, reference may be made to the literature [Remington's Pharmaceutical Sciences (19th ed., 1995)] and the like. The literature is considered a part of the present specification.

The antibody or composition of the present invention may be administered to a patient in a therapeutically effective amount or in a pharmaceutically effective amount.

As used herein, the term "administration" means introducing a predetermined substance to a subject by an appropriate method, and the composition may be administered through any general route as long as it may reach a target tissue. The route of administration may include intraperitoneal administration, intravenous administration, intramuscular administration, subcutaneous administration, intradermal administration, topical administration, intranasal administration, and intrarectal administration, but is not limited thereto.

Herein, "therapeutically effective amount" or "pharmaceutically effective amount" refers to an amount of an antibody or composition effective for preventing or treating a target disease, and means an amount that is sufficient to treat a disease with a reasonable benefit/risk ratio applicable to medical treatment and does not cause side effects. The level of the effective amount may be determined according to the patient's health condition, the type and severity of the disease, the activity of the drug, the sensitivity to the drug, administration method, administration time, the route of administration and excretion rate, treatment duration, factors including the combined or concurrently used drugs, and other factors well known in the medical field.

Specifically, the effective amount of the antibody in the composition of the present invention may vary depending on the age, sex, and body weight of the patient, and in general, may be administered from about 0.1 mg to about 1,000 mg, or from about 5 mg to about 200 mg per kg of body weight daily or every other day or may be divided into 1 to 3 times a day. However, since it may be increased or decreased depending on the route of administration, the severity of the disease, sex, body weight, age, and the like, the scope of the present invention is not limited thereto.

The term "subject" refers to a subject to which the composition of the present invention may be applied (prescribed), and may be a mammal, such as a rat, a mouse, or a livestock, including a human. Preferably, it may be a human, but is not limited thereto.

The antibody of the present invention or a pharmaceutical composition comprising the same may be administered as an individual therapeutic agent or in combination with other therapeutic agents, may be administered sequentially or simultaneously with conventional therapeutic agents, or may be administered singly or multiple times. In this case, the other therapeutic agents may further include any compound or natural extract known to have anticancer activity and safety has already been verified for the enhancement and reinforcement of anticancer activity.

Taking all of the above factors into consideration, it is important to administer an amount that may obtain the maximum effect with the minimum amount of side effects or without side effects, which may be easily determined by those of ordinary skill in the art.

In another aspect of the present invention, there is provided the use of an antibody specific for IGSF1 or a fragment thereof for the manufacture of a medicament for preventing or treating cancer, wherein the anti-IGSF1 antibody and fragment thereof, cancer, prevention and treatment are the same as described above.

In another aspect of the present invention, there is provided the use of an antibody specific for IGSF1 or a fragment thereof for the prevention and treatment of cancer, wherein the anti-IGSF1 antibody and fragment thereof, cancer, prevention and treatment are the same as described above.

In another aspect of the present invention, there is provided a method for preventing and treating cancer, comprising administering to a subject an antibody specific for IGSF1 or a fragment thereof, wherein the anti-IGSF1 antibody and fragment thereof, cancer, administration, treatment and prevention are the same as described above.

The subject may be a mammal, preferably a human. In addition, the subject may be a cancer patient or a subject who is highly likely to suffer from cancer.

The route of administration, dosage, and frequency of administration of the antibody specific for IGSF1 or fragment thereof may vary depending on the patient's condition and the presence or absence of side effects, and thus the antibody specific for IGSF1 or fragment thereof may be administered to a subject in various ways and amounts. The optimal administration method, dosage, and frequency of administration may be selected in an appropriate range by those of ordinary skill in the art. In addition, the antibody specific for IGSF1 or fragment thereof may be administered in combination with other drugs or physiologically active substances whose therapeutic effect is known with respect to cancer, or may be formulated in the form of combination preparations with other drugs.

MODE FOR CARRYING OUT THE INVENTION

Hereinafter, the present invention will be described in more detail by way of the following examples. However, the following examples are only for illustrating the present invention, and the scope of the present invention is not limited to the following examples.

Example 1. Construction of Anti-IGSF1 Antibody

Example 1.1. Expression and Purification of IGSF1 Antigen

Only the extracellular domain of IGSF1 was amplified in the Jurkat cell cDNA library through PCR method, and then the human Fc (fragment crystallizable region) and His-tag were fused at the carboxy terminus (C-terminus) using the N293F vector (YBiologics Co., Ltd.) to construct an IGSF1 protein expression vector. The HEK293F cells were transfected with the constructed IGSF1 expression vector and then cultured for 6 days in a medium to which 1 mM valporic acid (valproate) was added. Then, the IGSF1 extracellular domain was subjected to primary purification using protein A agarose, and then the IGSF1 extracellular domain was subjected to secondary purification using SUPER-DEX™ 200 gel filtration chromatography, and then used for antibody screening.

Example 1.2. Screening of IGSF1 Human Antibody

After coating and blocking of the IGSF1 antigen, bio-panning (YBiologics Co., Ltd.) was performed using the prepared human antibody library phages (YBiologics Co., Ltd.) to elute only the phages that were specifically bound to the antigen. The second and third rounds of bio-panning were performed with the phage amplified in the first round of bio-panning. ELISA was performed to confirm the specificity with the antigen for the positive phage antibody pool obtained through each round of bio-panning. In addition, it was confirmed that the anti-IGSF1 antibody was enriched in the phage pool obtained through the third round. Hundred types of monoclones with high binding capacity were selected from the third round of panning in each polyphage ELISA, and they were used to confirm whether they specifically bind to IGSF1 through ELISA analysis, thereby obtaining preliminary antibody clones. The screened preliminary antibody clones were subjected to DNA nucleotide sequencing to select 99 types of phages having different nucleotide sequences. It was confirmed that the selected 99 positive phage clones strongly bound to the antigen IGSF1, but did not bind to other antigens. Through the above method, as a result of screening antibodies that show specificity for the IGSF1 antigen using various other antigens, a total of 95 types could be selected.

Example 1.3. Confirmation of Specificity for IGSF1 Antigen

The selected antibodies were compared and analyzed for the specificity for other antigens including IGSF1 by ELISA method. It was confirmed that whether phage clones bind to various types of unspecified antigens such as mFc, hRAGE-Fc, CD58-Fc, and ITGA6-Fc, which were control antigens. The antibodies thus obtained were converted from phage to an IgG whole vector, and it was confirmed that the heavy chain sequence and the light chain sequence of the converted 95 clones matched the sequence of the phage antibody. Among the obtained antibodies, the most optimized antibody was selected, and it was referred to as "WM-A1-3389." The CDR sequences of the WM-A1-3389 antibody are shown in Table 1 below.

TABLE 1

| WM-A1-3389 | | |
| --- | --- | --- |
| CDR | Amino acid sequence | SEQ ID NO |
| H-CDR1 | GGTFSTYA | 1 |
| H-CDR2 | IIPFVGTV | 2 |
| H-CDR3 | VRDGGRSYFDS | 3 |
| L-CDR1 | TSNIGSNL | 4 |
| L-CDR2 | DNH | 5 |
| L-CDR3 | VAWDDSLNGYV | 6 |

Example 1.4. Production of WM-A1-3389 Antibody

In order to produce the WM-A1-3389 antibody, a polynucleotide (SEQ ID NO: 23) encoding a heavy chain (SEQ ID NO: 21) was loaded into the N293F vector (YBiologics Co., Ltd.) (hereinafter referred to as 'HC DNA'). In addition, a polynucleotide (SEQ ID NO: 24) encoding a light chain (SEQ ID NO: 22) was loaded into the N293F vector (YBiologics Co., Ltd.) (hereinafter referred to as LC DNA). The vector was transformed into the cells, and then the WM-A1-3389 antibody was obtained and purified. The purified protein was identified by SDS-PAGE.

TABLE 2

|  | Amino acid sequence | SEQ ID NO |
|---|---|---|
| Heavy chain | QVQLVQSGAEVKRPGSSVKVSCKASGGTFSTYAISWV RQAPGQGLEWMGRIIPFVGTVDYAQKFQDRVTITADK STNTAYMELSSLRSEDTAVYYCVRDGGRSYFDSWGPG ILVTVSSASTKGPSVFPLAPSSKSTSGGTAALGCLVKDY FPEPVTVSWNSGALTSGVHTFPAVLQSSGLYSLSSVVT VPSSSLGTQTYICNVNHKPSNTKVDKKVEPKSCDKTHT CPPCPAPELLGGPSVFLFPPKPKDTLMISRTPEVTCVVV DVSHEDPEVKFNWYVDGVEVHNAKTKPREEQYNSTY RVVSVLTVLHQDWLNGKEYKCKVSNKALPAPIEKTIS KAKGQPREPQVYTLPPSREEMTKNQVSLTCLVKGFYPS DIAVEWESNGQPENNYKTTPPVLDSDGSFFLYSKLTVD KSRWQQGNVFSCSVMHEALHNHYTQKSLSLSPGK | 21 |
| Light chain | QFVLTQPPSVSAAPGQDVIISCSGNTSNIGSNLVSWFQQ FPETAPKLLIYDNHKRPSGISDRFSGTKSGTSASLAISGL QSEDEADYYCVAWDDSLNGYVFGTGTKVTVLRTVAA PSVFIFPPSDEQLKSGTASVVCLLNNFYPREAKVQWKV DNALQSGNSQESVTEQDSKDSTYSLSSTLTLSKADYEK HKVYACEVTHQGLSSPVTKSFNRGEC | 22 |

Example 2. Analysis of Relationship Between IGSF1 Expression and Tumor-Infiltrating Lymphocytes

Example 2.1. Construction of IGSF1 Overexpressing Cell Line

Figure 1:
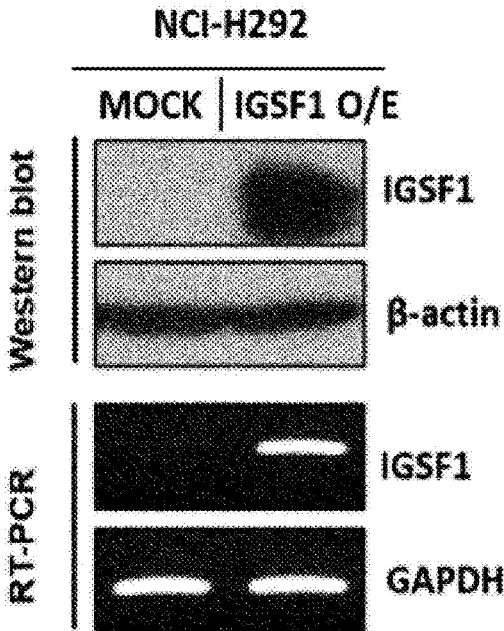
FIG. 1 illustrates a result obtained by confirming the expression level of IGSF1 in IGSF1 overexpressing human lung cancer cells (NCI-H292 IGSF1 O/E) and the control (NCI-H292 MOCK) through Western blot and RT-PCR.

IGSF1 was overexpressed in the human lung cancer cell line NCI-H292 or the human embryonic kidney cell line HEK293E cells to construct a cell line in which IGSF1 is overexpressed (FIG. 1). In this case, MOCK is a control without IGSF1 expression.

Specifically, an expression vector (OriGene Technologies, Inc., Cat No. RC209621) comprising a polynucleotide encoding IGSF1 was transfected into the human lung cancer cell line NCI-H292 cells or the human embryonic kidney cell line HEK293F cells. Thereafter, the transfected cells were selected by culturing them in a medium containing G418 (neomycin). The expression level of IGSF1 was checked for the selected clones, and the clone showing the highest IGSF1 expression was selected and used for the experiment. MOCK refers to an empty vector into which a polynucleotide encoding IGSF1 is not loaded.

Example 2.2. Analysis of Relationship Between IGSF1 Expression and Tumor-Infiltrating Lymphocytes in Lung Cancer Cell Line Spheroids In order to confirm the correlation between IGSF1 expression and tumor-infiltrating lymphocytes (TIL) in lung cancer at a cellular level, tumor-infiltrating lymphocytes were identified in spheroids using lung cancer cells in which IGSF1 was overexpressed.

First, in order to construct lung cancer cell spheroids, NCI-H292 IGSF1 O/E cells and NCI-H292 MOCK cells were seeded in a U-Bottom 96-well plate (Nunc, 174925) to 2×10+ cells/well, respectively, and cultured for 72 hours in a carbon dioxide incubator at 37° C. Peripheral blood mononuclear cells (PBMC) were prepared by removing the supernatant by centrifugation at 1,200 rpm for 10 minutes and resuspending in PBS. 18 µl of DMSO was added to CFSE (carboxyfluorescein succinimidyl ester, Invitrogen, C34554) to a concentration of 5 mM and diluted in PBS to 1 mM. 1 µl of 1 mM CFSE solution was added per $1\times10^{6}$ cells/ml of the prepared peripheral blood mononuclear cells and then stained in a carbon dioxide incubator at 37° C. for 10 minutes. Then, a medium containing FBS (fetal bovine serum) in an amount of 5 times the amount of PBS was added to a solution containing the stained peripheral blood mononuclear cells (PBMC). Thereafter, the reaction was carried out in a carbon dioxide incubator at 37° C. for 5 minutes. The supernatant was removed by centrifugation at 1,200 rpm for 10 minutes, and then the stained peripheral blood mononuclear cells were resuspended in a medium to prepare peripheral blood mononuclear cells for use in the experiment.

Thereafter, the formed spheroids were transferred to an ultra-low adhesion 96-well plate (Corning, CLS3474) by 2 wells, and then seeded with peripheral blood mononuclear cells, which were stained with CFSE, to $1\times10^{5}$ cells/well, and co-cultured in a carbon dioxide incubator at 37° C. for 24 hours. Tumor-infiltrating lymphocytes (TIL) were observed under a fluorescence microscope. In this case, the NCI-H292 MOCK cells were used as a control for IGSF1 overexpressing cells.

Figure 2:
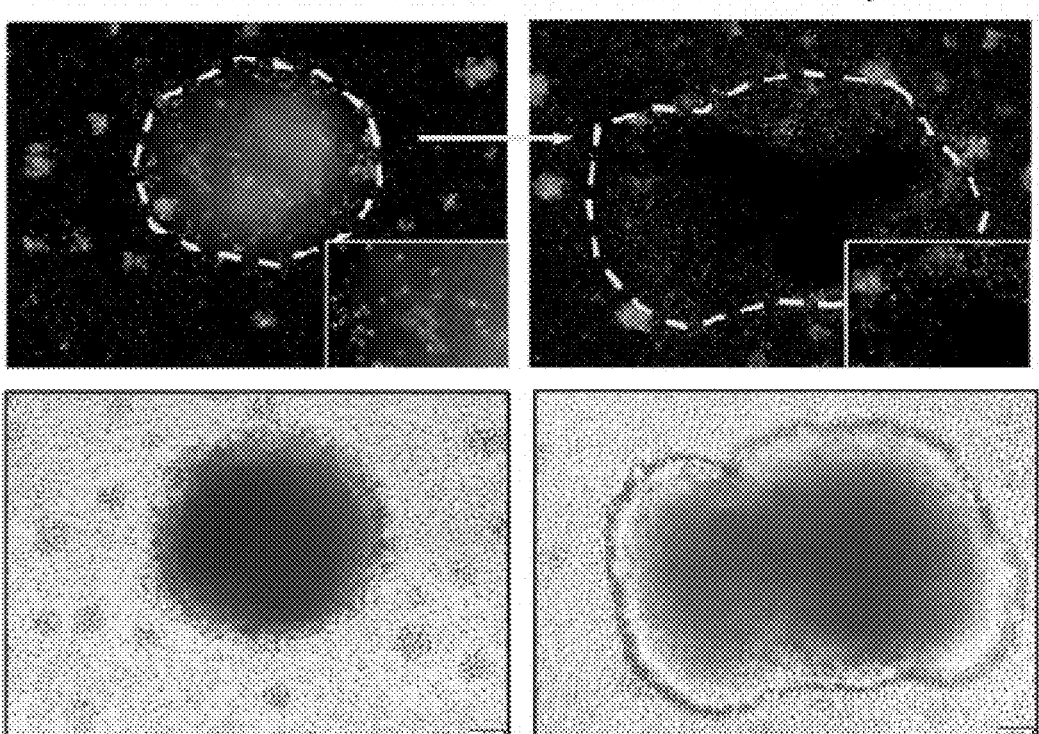
FIG. 2 illustrates a result obtained by confirming tumor-infiltrating lymphocytes (TIL) present in the spheroids when IGSF1 overexpressing human lung cancer cells (NCI-H292

As a result, it was confirmed that tumor-infiltrating lymphocytes (TIL) were decreased in IGSF1 overexpressing human lung cancer cell (NCI-H292 IGSF1 O/E) spheroids compared to the control (NCI-H292 MOCK) (FIG. 2).

Example 2.3. Analysis of Relationship Between IGSF1 Expression and Tumor-Infiltrating Lymphocytes in Tumor Tissues of Humanized Mice Transplanted with Lung Cancer Cell Lines In order to confirm the correlation between the expression of IGSF1 and tumor-infiltrating lymphocytes (TIL) in lung cancer at an in vivo level, tumor-infiltrating lymphocytes were identified in the tumor tissues of humanized mice transplanted with human lung cancer cells in which IGSF1 was overexpressed.

Specifically, NCI-H292 IGSF1 O/E cells, an IGSF1 over-expressing human lung cancer cell line, or NCI-H292 MOCK cells, a control, were transplanted at 5×10⁶ cells per animal into NSG mice (SID (NSGA) mice, F) transplanted with human peripheral blood mononuclear cells (PBMC), and then tumor sections from the mice were collected on day 17.

Human peripheral blood mononuclear cells were isolated from each collected tumor, analyzed by FACS, and tumor-infiltrating lymphocytes and the expression level of IGSF1 in the tumor tissue were confirmed by immunohistochem-istry staining of the tumor tissue. In order to identify the human peripheral blood mononuclear cells infiltrating the tumor, first, the tumor tissue was treated with collagenase B (Roche, cat. #11088815001) and reacted at 37° C. for 2 hours or more to dissociate the tumor tissue. When the tumor tissue was completely dissociated into cells, it was isolated into single cells by pipetting with a 1 ml pipette.

The isolated single cells were transferred to a 50 ml tube (SPL, cat. #50050) and then washed with 20 ml of PBS. Thereafter, the supernatant was removed by centrifugation at 1,200 rpm for 3 minutes. The remaining cells were reacted with DNase I (Roche, cat. #11284932001) at 37° C. for 20 minutes. Thereafter, 20 ml of PBS was added, and the supernatant was removed by centrifugation at 1,200 rpm for 3 minutes. The remaining cells were treated with 0.25% Trysin/EDTA (GIBCO, cat. #15400-054). The cells were mixed well, and then a cell strainer (SPL, cat. #93070) was placed on a new 50 ml tube, and the cells were filtered. 20 ml of PBS was added to the tube containing the filtered cells and mixed well. Thereafter, the supernatant was removed by centrifugation at 1,200 rpm for 3 minutes, and then 1 ml of Stain Buffer (BD, cat. #554656) was added to the remaining cells and washed.

In order to block the non-specific antibody reaction of the isolated cells, 2 μg of human Fc block (BD, cat. #564219) was added and reacted for 10 minutes at room temperature. After the reaction, an anti-human CD45 (BD, cat. #564357) antibody was added and reacted at 4° C. for 30 minutes while blocking the light. After the reaction, 1 ml of Stain Buffer was added and washed. Thereafter, the supernatant was removed by centrifugation at 1,200 rpm for 3 minutes, and the cells were collected, and then 200 μl of Stain Buffer was added and analyzed by a BD LSRFortessa™ flow cytometer (FIG. 3).

In addition, the distribution of tumor lymphocytes expressed in the tumor and the expression of IGSF1 were confirmed by immunohistochemistry staining method. Spe-cifically, NCI-H292 IGSF1 O/E cells, a human lung cancer cell line, or NCI-H292 MOCK cells were transplanted at 5×10⁶ cells per animal into NSG mice (SID (NSGA) mice, F) transplanted with human peripheral blood mononuclear cells (PBMC). Thereafter, on day 17, sections of the tumor tissue collected from mice were deparaffinized and rehy-drated.

Thereafter, it was soaked in a target repair buffer and heated in a microwave for 15 minutes for heat-induced epitope repair. Then, it was placed in a target repair buffer for 30 minutes, and then washed 3 times with Tris buffered saline-0.05% Tween 20 (TBS-T), and blocked with a block-ing solution for 60 minutes. The primary antibody was an anti-IGSF1 antibody (Santacruz, sc-393786), which was 1:100 diluted and allowed to be bound overnight at 4° C. The next day, it was washed 3 times with TBS-T, and reacted with an endogenous peroxidase blocking reagent (Cell Marque, 925B) at room temperature for 5 minutes, and then the secondary antibody (Vector, PK-6101 PK-6102) was allowed to be bound at room temperature for 60 minutes. It was washed 3 times with TBS-T and then reacted with avidin-biotin for 60 minutes. The final DAB staining (Vec-tor, SK-4100) was performed, and then the tissue staining was finished through a dehydration process, and the stained tissue sections were observed under a microscope.

As a result, it was confirmed that hCD45+ cells, which are human immune cells, were reduced in the tumor tissue of humanized mice transplanted with IGSF1 overexpressing human lung cancer cells (NCI-H292 IGSF1 O/E) compared to the control (NCI-H292 MOCK) (FIG. 4).

Example 3. Analysis of Binding Affinity of Anti-IGSF1 Antibody

Example 3.1. Analysis of Binding Affinity of Anti-IGSF1 Antibody at In Vitro The binding affinity of the WM-A1-3389 antibody to the IGSF1 antigen was confirmed at an in vitro using ELISA analysis.

Specifically, it was treated with 100 ng of IGSF1 to coat a 96-well plate, and then 200 μl of 4% skim milk (PBST) was added and blocked at room temperature for 1 hour. The WM-A1-3389 antibody was serially diluted to 12 concen-trations by ⅓ in 4% skim milk (PBST), treated, and then reacted at room temperature for 2 hours. After the reaction was completed, the wells were washed with PBST, treated with human IgG Fc-HRP antibody, and reacted at room temperature for 1 hour. Then, the wells were washed with PBST, and then TMB peroxidase substrate was added to confirm the degree of color development, and then absor-bance was measured at 450 nm, and the results were compared and analyzed.

As a result, the WM-A1-3389 antibody had a Kd value of about $2.2 \times 10^{-11}$, indicating that it had a high binding affinity to the IGSF1 antigen (FIG. 5).

Example 3.2. Analysis of Binding Affinity of Anti-IGSF1 Antibody to IGSF1 in Cells In order to confirm the binding affinity of the WM-A1-3389 antibody to the IGSF1 antigen at a cellular level, the binding capacity of the WM-A1-3389 antibody to IGSF1 was confirmed using IGSF1 overexpressing human lung cancer cells (NCI-H292 IGSF1 O/E) and the control (NCI-H292 MOCK).

Specifically, the medium of NCI-H292 IGSF1 O/E cells and NCI-H292 MOCK cells was removed, washed once with PBS, and then treated with 2 ml of 0.25% trypsin-EDTA, and the cells were isolated. The isolated cells were diluted with 8 ml of PBS (hereinafter referred to as FACS buffer) containing 2% FBS and 0.05% sodium azide, and then the supernatant was removed by centrifugation at 1,200 rpm for 1 minute. Then, the cells were resuspended in FACS buffer to 1×10⁵ cells/ml. Thereafter, 1 ml of each was dispensed in a FACS tube, and the supernatant was removed by centrifugation at 1,200 rpm for 1 minute.

The pellet remaining in the FACS tube was released by vortexing, and the WM-A1-3389 antibody was diluted by ¼ from 20 μM to 0 μM per 200 μl of FACS buffer, added to a total of 12 concentrations, and then reacted at 4° C. for 30 minutes. After the reaction was completed, 1 ml of FACS buffer was added to each tube, and the supernatant was removed by centrifugation at 1,200 rpm for 1 minute. This process was performed a total of two times. The pellet remaining in the FACS tube was released by vortexing, and 5 µg/ml of FITC-labeled goat anti-human IgG antibody (Invitrogen, 62-8411) was added per 200 µl of FACS buffer and reacted while blocking the light at 4° C. for 30 minutes. After the reaction was completed, 1 ml of FACS buffer was added to each tube, and the supernatant was removed by centrifugation at 1,200 rpm for 1 minute. This process was performed a total of two times.

Finally, after removal of the supernatant, the remaining pellet was resuspended in 200 µl of FACS buffer and analyzed by FACS. For FACS analysis, FITC fluorescence value labeled in each cell was measured using a BD LSR-Fortessa™ flow cytometer, and then the results were analyzed using a FLOWJO™ software, and EC50 value was calculated using a sigma plot program. In this case, NCI-H292 MOCK cells were used as a control for IGSF1 overexpressing cells.

As a result, binding was not confirmed in the control (NCI-H292 MOCK) regardless of the concentration of the WA-A1-3389 antibody. On the other hand, in human lung cancer cells in which IGSF1 is overexpressed (NCI-H292 IGSF1 O/E), the EC50 value of the WM-A1-3389 antibody was confirmed to be about 69 nM (FIG. 6).

Example 4. Analysis of Antigen Specificity of Anti-IGSF1 Antibody for IGSF1 Antigen in Cells In order to analyze the antigen specific binding capacity (target selectivity) of the WM-A1-3389 antibody to the IGSF1 antigen at a cellular level, binding of the WM-A1-3389 antibody to IGSF1 expressed in cells was confirmed using human lung cancer cells in which IGSF1 is overexpressed (NCI-H292 IGSF1 O/E).

Specifically, the medium of human lung cancer cells in which IGSF1 is overexpressed (NCI-H292 IGSF1 O/E) and a control thereof (NCI-H292 MOCK) was removed, washed once with PBS, and then treated with 2 ml of 0.25% trypsin-EDTA, and the cells were isolated. The isolated cells were diluted with 8 ml of PBS containing 2% FBS and 0.05% sodium azide (hereinafter referred to as FACS buffer), and then the supernatant was removed by centrifugation at 1,200 rpm for 1 minute. Then, the cells were resuspended in FACS buffer to $1 \times 10^5$ cells/ml. Thereafter, 1 ml of each was dispensed in a FACS tube, and the supernatant was removed by centrifugation at 1,200 rpm for 1 minute.

The pellet remaining in the FACS tube was released by vortexing, and 0.4 µg of the human IgG isotype antibody (Bio X cell, BE0297) or the WM-A1-3389 antibody was added per 200 µl of FACS buffer, and then reacted at 4° C. for 30 minutes. After the reaction was completed, 1 ml of FACS buffer was added to each tube, and the supernatant was removed by centrifugation at 1,200 rpm for 1 minute. This process was performed a total of two times. The cell pellet remaining in the FACS tube was released by vortexing, and 0.4 µg of FITC-labeled goat anti-human IgG antibody (Invitrogen, 62-8411) was added per 200 µl of FACS buffer and reacted while blocking the light at 4° C. for 30 minutes.

After the reaction was completed, 1 ml of FACS buffer was added to each tube, and the supernatant was removed by centrifugation at 1,200 rpm for 1 minute. Finally after removal of the supernatant, the remaining pellet was resuspended in 200 µl of FACS buffer and analyzed by FACS. For FACS analysis, FITC fluorescence value labeled in each cell was measured using a BD LSRFortessa™ flow cytometer, and the results were analyzed using a FLOWJO™ software. In this case, NCI-H292 MOCK cells were used as a control for IGSF1 overexpressing cells, and human IgG isotype was used as a control for the WM-A1-3389 antibody.

As a result, the group treated with the WM-A1-3389 antibody showed a binding capacity of about 2.6% in the control (NCI-H292 MOCK) and a binding capacity of about 78.9% in IGSF1 overexpressing cells (NCI-H292 IGSF1 O/E) compared to the group treated with the IgG isotype (FIG. 7).

Next, NCI-H292 IGSF1 O/E cells and HEK293E IGSF1 O/E cells in which IGSF1 is overexpressed were transfected with shRNA (hereinafter referred to as shIGSF1) that specifically binds to mRNA encoding IGSF1 to reduce the expression of IGSF1 (hereinafter referred to as IGSF1 K/D cells), and then the binding capacity of the WM-A1-3389 antibody to the IGSF1 antigen in the cells was measured. In this case, scramble RNA without shIGSF1 (hereinafter referred to as sc cell) was used as a control of transfection (IGSF1 K/D), and the human IgG isotype was used as a control for the WM-A1-3389 antibody. The antigen specificity of the WM-A1-3389 antibody was compared to the binding capacity in IGSF1 K/D cells based on the binding capacity in sc cells. In addition, NCI-H292 MOCK cells and HEK293E MOCK cells were used as controls for IGSF1 overexpressing cells, respectively.

Specifically, the media of NCI-H292 (IGSF1 O/E and MOCK) and HEK293E (IGSF1 O/E and MOCK) cell lines were removed and washed once with PBS, and then NCI-H292 cells were treated with 2 ml of 0.25% trypsin-EDTA, and HEK293E cells were treated with 2 ml of 0.05% trypsin-EDTA, respectively, and the cells were isolated. The isolated cells were diluted with 8 ml of culture medium, and then the supernatant was removed by centrifugation at 800 rpm for 3 minutes. The remaining cells were resuspended to a concentration of $1 \times 10^5$ cells/ml (NCI-H292) and $0.5 \times 10^5$ cells/ml (HEK293E), respectively, and then 3 ml of the cells was added to a 60 mm culture plate, and cultured in a cell incubator at 37° C. for one day. The next day, shIGSF1 transfection was performed. 200 µl of jet PRIME buffer and 10 nM of shIGSF1 were added and mixed in a 1.5 ml tube, and then 4 µl of jet PRIME reagent was added, mixed, and reacted at room temperature for 10 minutes. Then, the medium of the cells prepared the day before was replaced, and then 200 µl of the transfection mixture was added to each cell and reacted in a cell incubator for 24 hours. After 24 hours, it was replaced with a fresh culture medium and further cultured for 24 hours.

For the transfected cells, the medium was removed, and FACS analysis was performed in the same manner as above.

As a result, the binding of the WM-A1-3389 antibody compared to the group treated with the human IgG isotype was confirmed in the sc cell line. In addition, when the IGSF1 expression was reduced based on the binding capacity (IGSF1 K/D cells), it was confirmed that the binding capacity of the WM-A1-3389 antibody was reduced together (FIG. 8).

Example 5. Analysis of Immuno-Anticancer Efficacy of Anti-IGSF1 Antibody in Lung Cancer Cell Spheroids In order to analyze the immuno-anticancer efficacy of the WM-A1-3389 antibody at a cellular level, lung cancer cell spheroids and peripheral blood mononuclear cells (PBMC)

were co-cultured to confirm death of tumor-infiltrating lymphocytes (TIL) and immunogenic cell.

Co-culture of lung cancer cell spheroids and peripheral blood mononuclear cells was performed in the same manner as in Example 2.2.

The co-cultured cells and the supernatant were collected in a tube, and the supernatant was removed by centrifugation at 1,200 rpm for 2 minutes. The cell pellet was made into single cells by treatment with 500 μl of 0.25% trypsin-EDTA and then diluted with 2 ml of PBS containing 2% FBS and 0.05% $NaN_3$ (hereinafter referred to as FACS buffer), and then the supernatant was removed by centrifugation at 1,200 rpm for 3 minutes. The remaining cell pellet was resuspended in 200 μl of FACS buffer, and then anti-HMGB1 antibody (Biolegend, 651408) and anti-Hsp90 antibody (Enzo Life Science, ADI-SPA-830PE-D) were added and stained at 4° C. for 30 minutes.

1 ml of FACS buffer was added to each tube, and the supernatant was removed by centrifugation at 1,200 rpm for 2 minutes. This process was repeated a total of two times. Thereafter, analysis was performed using a BD LSR-Fortessa™ flow cytometer. The results of FACS analysis were analyzed using a FLOWJO™ software. In addition, tumor-infiltrating lymphocytes (TIL) were observed under a fluorescence microscope. In this case, the human IgG isotype was used as a control for the WM-A1-3389 antibody.

As a result, it was confirmed that tumor-infiltrating lymphocytes (TIL) were increased in the group treated with the WM-A1-3389 antibody compared to the control in IGSF1 overexpressing lung cancer cell (NCI-H292 IGSF1 O/E) spheroids (FIG. 9). In addition, it was confirmed that immunogenic cell death (ICD) was also increased in the group treated with the WM-A1-3389 antibody compared to the control in IGSF1 overexpressing lung cancer cell spheroids (FIG. 10).

Example 6. Analysis of Tumor Growth Inhibition Efficacy of Anti-IGSF1 Antibody in Allograft Mouse Model In order to confirm the anticancer efficacy of the WM-A1-3389 antibody at an animal level, peripheral blood mononuclear cell humanized model (PBMC humanized model) mice were transplanted with human lung cancer cells in which IGSF1 is overexpressed (NCI-H292 IGSF1 O/E), and then the tumor growth inhibition efficacy of the WM-A1-3389 antibody was evaluated.

Specifically, 6-week-old female peripheral blood mononuclear cell humanized mice (Gem biosciences) were purchased and acclimatized for 1 week, and then IGSF1 overexpressing human lung cancer cells NCI-H292 IGSF1 O/E ($5×10^6$ cells/animal) were diluted in PBS and Matrigel and injected subcutaneously (200 μl) into the right dorsal side of the mice. When the tumor size reached about 120 $mm^3$, IgG isotype (control) or the WM-A1-3389 antibody was administered intraperitoneally at a dose of 10 mg/kg, respectively. Administration was performed once every 3 days for 4 weeks, and the tumor size and body weight of the mice were measured twice a week. On day 22 of administration, blood and tumors from the satellite group mice were obtained and subjected to FACS analysis. After the administration was completed, the experimental animals were euthanized, the tumors were extracted, and the weight was measured. The human IgG isotype was used as a control for the WM-A1-3389 antibody.

As a result, the group administered with the WM-A1-3389 antibody exhibited high tumor growth inhibition efficacy compared to the control, and exhibited a tumor inhibition rate (TGI) of about 64.5% (FIG. 11). In addition, it was confirmed that tumor growth was inhibited even for individual subjects (FIG. 12).

Example 7. Analysis of IGSF1 Expression in Caucasian Lung Cancer Patient Tissue The expression of IGSF1 in Caucasian lung cancer patient tissue was confirmed by immunohistochemistry staining method.

Specifically, a section of the tissue of the human non-small cell lung cancer patient was deparaffinized and rehydrated, and then soaked in a target repair buffer, and then heated in a microwave for 15 minutes for heat-induced epitope repair. Thereafter, it was reacted in a target repair buffer for another 30 minutes. Thereafter, it was washed 3 times with Tris buffered saline with 0.05% Tween 20 (TBS-T), and then blocked with a blocking solution for 60 minutes. The primary antibody was an anti-IGSF1 antibody (Santacruz, sc-393786), which was 1:100 diluted and allowed to be bound overnight at 4° C. The next day, the tissue section was washed 3 times with TBS-T and then reacted with an endogenous peroxidase blocking reagent (Cell Marque, 925B) for 5 minutes. Then, the secondary antibody (Vector, PK-6101 PK-6102) was allowed to be bound at room temperature for 60 minutes. Thereafter, it was washed 3 times with TBS-T, treated with avidin-biotin, and reacted for 60 minutes, and then the DAB staining (Vector, SK-4100) was performed. The stained tissue section was observed under a microscope (FIG. 13).

The invention claimed is:

1. An antibody specific for IGSF1 or a fragment thereof, comprising a heavy chain variable region comprising H-CDR1 of SEQ ID NO: 1, H-CDR2 of SEQ ID NO: 2 and H-CDR3 of SEQ ID NO: 3; and a light chain variable region comprising L-CDR1 of SEQ ID NO: 4, L-CDR2 of SEQ ID NO: 5 and L-CDR3 of SEQ ID NO: 6.

2. The antibody specific for IGSF1 or fragment thereof according to claim 1, wherein the heavy chain variable region has the amino acid sequence of SEQ ID NO: 7; and the light chain variable region has the amino acid sequence of SEQ ID NO: 8.

3. A polynucleotide encoding a heavy chain variable region comprising H-CDR1 of SEQ ID NO: 1, H-CDR2 of SEQ ID NO: 2 and H-CDR3 of SEQ ID NO: 3.

4. A polynucleotide encoding a light chain variable region comprising L-CDR1 of SEQ ID NO: 4, L-CDR2 of SEQ ID NO: 5 and L-CDR3 of SEQ ID NO: 6.

5. An expression vector comprising the polynucleotide according to claim 3.

6. An expression vector comprising the polynucleotide according to claim 4.

7. A transformed cell into which the expression vector according to claim 5 is introduced.

8. A transformed cell into which the expression vector according to claim 6 is introduced.

9. A method of producing an antibody specific for IGSF1 or a fragment thereof, comprising:

i) culturing the transformed cell according to claim 7; and ii) recovering the antibody specific for IGSF1 or the fragment thereof.

10. A method of producing an antibody specific for IGSF1 or a fragment thereof, comprising:

i) culturing the transformed cell according to claim 8; and ii) recovering the antibody specific for IGSF1 or the fragment thereof.

11. A method for treating cancer, the method comprising administering to a subject the antibody specific for IGSF1 or fragment thereof according to claim 1.

12. The method according to claim 11, wherein the cancer is one in which IGSF1 is overexpressed.

13. The method according to claim 11, wherein the cancer is any one selected from the group consisting of gastric cancer, liver cancer, lung cancer, non-small cell lung cancer, colorectal cancer, bladder cancer, bone cancer, blood cancer, breast cancer, melanoma, thyroid cancer, parathyroid cancer, bone marrow cancer, rectal cancer, throat cancer, laryngeal cancer, esophageal cancer, pancreatic cancer, tongue cancer, skin cancer, brain tumor, uterine cancer, head or neck cancer, gallbladder cancer, oral cancer, perianal cancer, colon cancer, and central nervous system tumor.

14. A pharmaceutical composition comprising the antibody specific for IGSF1 or fragment thereof according to claim 1 as an active ingredient.

\* \* \* \* \*